(12) United States Patent
Avidor et al.

(10) Patent No.: US 10,631,745 B2
(45) Date of Patent: Apr. 28, 2020

(54) SYSTEM AND METHOD FOR DETERMINING BLOOD FLOW

(75) Inventors: Yoav Avidor, Tel-Aviv (IL); Baruch Levy, Beer-Yaacov (IL); Dan Avidor, Tel-Aviv (IL); Daniel Burkhoff, West Harrison, NY (US)

(73) Assignee: Cheetah Medical, Inc., Wilmington, DE (US)

( * ) Notice: Subject to any disclaimer, the term of this patent is extended or adjusted under 35 U.S.C. 154(b) by 34 days.

(21) Appl. No.: 13/120,159

(22) PCT Filed: Sep. 22, 2009

(86) PCT No.: PCT/IL2009/000916
§ 371 (c)(1),
(2), (4) Date: Mar. 22, 2011

(87) PCT Pub. No.: WO2010/032252
PCT Pub. Date: Mar. 25, 2010

(65) Prior Publication Data
US 2011/0178418 A1   Jul. 21, 2011

Related U.S. Application Data

(60) Provisional application No. 61/136,640, filed on Sep. 22, 2008.

(51) Int. Cl.
*A61B 5/0245* (2006.01)
*A61B 5/053* (2006.01)
(Continued)

(52) U.S. Cl.
CPC ............ *A61B 5/0245* (2013.01); *A61B 5/026* (2013.01); *A61B 5/0295* (2013.01); *A61B 5/053* (2013.01);
(Continued)

(58) Field of Classification Search
CPC ....... A61B 5/0535; A61B 5/028; A61B 5/021; A61B 5/026; A61B 5/022
(Continued)

(56) References Cited

U.S. PATENT DOCUMENTS

| 3,730,171 A | 5/1973 | Namon |
| 5,235,976 A | 8/1993 | Spinelli |

(Continued)

FOREIGN PATENT DOCUMENTS

| CN | 101160091 | 4/2008 |
| WO | WO 2004/098376 | 11/2004 |

(Continued)

OTHER PUBLICATIONS

Office Action dated Feb. 12, 2013 From the Israel Patent Office Re. Application No. 211870 and Its Translation Into English.
(Continued)

*Primary Examiner* — Jacqueline Cheng
*Assistant Examiner* — Tho Q Tran

(57) ABSTRACT

A method of diagnosis is disclosed. The method comprises: acquiring an absolute component and a phase component of an input signal indicative of an impedance of an organ of a subject; determining baseline blood flow of the subject based on the phase component; determining transient changes in blood flow based on at least the absolute component; and displaying the baseline blood flow and the transient changes in blood flow.

15 Claims, 12 Drawing Sheets

(51) Int. Cl.
    A61B 5/026    (2006.01)
    A61B 5/0295   (2006.01)
    G16H 40/63    (2018.01)
    A61B 5/00     (2006.01)
    A61B 5/02     (2006.01)
(52) U.S. Cl.
    CPC .......... *G16H 40/63* (2018.01); *A61B 5/02007* (2013.01); *A61B 5/02028* (2013.01); *A61B 5/7207* (2013.01)
(58) Field of Classification Search
    USPC ................................. 600/504–507, 481, 483
    See application file for complete search history.

(56) References Cited

U.S. PATENT DOCUMENTS

| | | | |
|---|---|---|---|
| 5,642,734 | A | 7/1997 | Ruben et al. |
| 6,485,431 | B1 | 11/2002 | Campbell |
| 2002/0095087 | A1* | 7/2002 | Mourad ............... A61B 5/0048 600/442 |
| 2004/0049120 | A1* | 3/2004 | Cao ..................... A61B 5/0456 600/521 |
| 2004/0220636 | A1* | 11/2004 | Burnes ............................. 607/17 |
| 2005/0101875 | A1* | 5/2005 | Semler et al. ................ 600/509 |
| 2005/0203428 | A1 | 9/2005 | Judy |
| 2005/0267381 | A1 | 12/2005 | Benditt et al. |
| 2006/0111642 | A1 | 5/2006 | Baum et al. |
| 2006/0235323 | A1* | 10/2006 | Hatib et al. ................... 600/526 |
| 2008/0009759 | A1* | 1/2008 | Chetham ....................... 600/526 |
| 2008/0058630 | A1 | 3/2008 | Robertson |
| 2008/0103407 | A1* | 5/2008 | Bolea .................. A61N 1/0556 600/529 |
| 2009/0062680 | A1* | 3/2009 | Sandford ........... A61B 5/04012 600/544 |

FOREIGN PATENT DOCUMENTS

| | | |
|---|---|---|
| WO | WO 2006/087696 | 8/2006 |
| WO | WO 2010/032252 | 3/2010 |

OTHER PUBLICATIONS

International Search Report and the Written Opinion dated Feb. 1, 2010 From the International Searching Authority Re.: Application No. PCT/IL09/00916.
International Preliminary Report on Patentability dated Mar. 31, 2011 From the International Bureau of WIPO Re. Application No. PCT/IL2009/000916.
Translation of Office Action dated Jul. 12, 2012 From the State Intellectual Property Office of the People's Republic of China Re. Application No. 200980136855.4.
Shu "Study on Impedance Blood Flow Measurement System Based on Miniature Electrodes", Thesis Submitted in Partial Fulfillment of the Requirements for the Degree of master of Biomedical Engineering, Huazhong University of Science & Technology, Wuhan, China, 70 P., May 2005.
Office Action dated Oct. 30, 2013 From the State Intellectual Property Office of the People's Republic of China Re. Application No. 200980136855.4 and Its Translation Into English.
Office Action dated Feb. 11, 2015 From the State Intellectual Property Office of the People's Republic of China Re. Application No. 200980136855.4 and Its Translation Into English.
Office Action dated Jul. 19, 2014 From The State Intellectual Property Office of the People's Republic of China Re. Application No. 200980136855.4 and Its Translation Into English.
Official Decision of Rejection dated May 30, 2014 From the Japanese Patent Office Re. Application No. 2011-527470 and Its Translation into English.
Supplementary European Search Report and the European Search Opinion dated Aug. 21, 2014 From the European Patent Office Re. Application No. 09814183.1.
Translation of Notice of Reason for Rejection dated Sep. 10, 2013 From the Japanese Patent Office Re. Application No. 2011-527470.
Patent Examination Report dated Sep. 9, 2013 From the Australian Government, IP Australia Re. Application No. 2009294179.
Patent Examination Report dated Aug. 29, 2013 From the Australian Government, IP Australia Re. Application No. 2009294179.
Translation of Office Action dated May 21, 2013 From the State Intellectual Property Office of the People's Republic of China Re. Application No. 200980136855.4.
Patent Examination Report dated Sep. 12, 2014 From the Australian Government, IP Australia Re. Application No. 2009294179.
Notice of Reason for Rejection dated Sep. 1, 2015 From the Japanese Patent Office Re. Application No. 2011-527470 and Its Translation Into English.
Office Action dated Apr. 29, 2015 From the State Intellectual Property Office of the People's Republic of China Re. Application No. 200980136855.4 and Its Translation Into English.
Communication Pursuant to Article 94(3) EPC dated Dec. 5, 2016 From the European Patent Office Re. Application No. 09814183.1. (4 Pages).
Examination Report Under Sections 12 & 13 of the Patents Act, 1970 and the Patents Rules, 2003 dated Mar. 14, 2018 From the Government of India, Intellectual Property India, Patents, Designs, Trade Marks, Geographical Indications Re. Application No. 249/MUMNP/2011. (8 Pages).
Hearing Notice dated Nov. 8, 2019 From the Government of India, Intellectual Property India, Patent Office, Intellectual Property Building Re. Application No. 249/MUMNP/2011. (4 Pages).
Tabrizchi et al. "Methods of Blood Flow Measurement in the Arterial Circulatory System", Journal of Pharmacological and Toxicological Methods, 44(2): 375-384, Sep.-Oct. 2000.

* cited by examiner

SYSTEM AND METHOD FOR DETERMINING BLOOD FLOW

RELATED APPLICATIONS

This application is a National Phase of PCT Patent Application No. PCT/IL2009/000916 having an International filing date of Sep. 22, 2009, which claims the benefit of priority of U.S. Provisional Patent Application No. 61/136,640 filed Sep. 22, 2008, the contents of which are hereby incorporated by reference as if fully set forth herein.

FIELD AND BACKGROUND OF THE INVENTION

The present invention, in some embodiments thereof, relates to diagnosis in medicine and, more particularly, but not exclusively, to system and method for determining blood flow by analyzing electrical signals received from a living body.

Technologies related to measurement of electrical properties of organs, such as the measurement of bioimpedance are generally known. Typically, such technologies relate to the monitoring of physiological parameters by extracting physiologically significant characteristics from electrical measurements, see, e.g., U.S. Pat. No. 6,577,897. Characteristics may include measures that aid in the discernment of physiological indications pertaining directly or indirectly to the state of organs (e.g., blood vessels, heart, lungs and the like), and reveal measures of various physiological conditions including critical life-threatening conditions.

For example, heart diseases may be caused by (i) a failure in the autonomic nerve system where the impulses from the central nervous system control to the heart muscle fail to provide a regular heart rate and/or (ii) an insufficient strength of the heart muscle itself where even though the patient has a regular heart rate, its force of contraction is insufficient. Either way, the amount of blood or the rate at which the blood is supplied by a diseased heart is abnormal and it is appreciated that an assessment of the state of a patient's circulation is of utmost importance.

The simplest measurements, such as heart rate and blood pressure, may be adequate for many patients, but if there is a cardiovascular or heamodynamic abnormality then more detailed measurements are needed.

Cardiac output (CO) is the volume of blood pumped by the heart during a time interval, which is typically taken to be a minute. Cardiac output is the product of heart rate (HR) and the amount of blood which is pumped with each heartbeat, also known as the stroke volume (SV). For example, the stroke volume at rest in the standing position averages between 60 and 80 ml of blood in most adults. Thus, at a resting heart rate of 80 beats per minute the resting cardiac output varies between 4.8 and 6.4 L per min.

A common clinical problem is that of hypotension (low blood pressure); this may occur because the cardiac output is low and/or because of low systemic vascular resistance. This problem can occur in a wide range of patients, especially those in intensive care or postoperative high dependency units. In these high risk patients, more detailed monitoring is typically established including measuring central venous pressure via a central venous catheter and continuous display of arterial blood pressure via a peripheral arterial catheter.

In addition to the above measurements, the measurement of cardiac output is useful. For example, when combined with arterial pressure measurements, cardiac output can be used for calculating the systemic vascular resistance. The measurement of cardiac output is useful both for establishing a patient's initial cardiovascular state and for monitoring the response to various therapeutic interventions such as transfusion, infusion of inotropic drugs, infusion of vasoactive drugs (to increase or reduce systemic vascular resistance) or altering heart rate either pharmacologically or by adjusting pacing rate.

Several methods of measuring cardiac output are presently known, representative Examples include the Fick method, described by Adolf Fick in 1870, the amount of oxygen taken up by the body during respiration and the difference in oxygen concentration between venous and arterial blood is used to calculate the cardiac output; the transoesophageal echocardiography (see, e.g., U.S. Pat. No. 6,142,941) in which cardiac output is derived from blood flow velocity (recorded via Doppler shift) cross-sectional area of the blood vessel and heart rate; and the compliance based method (see, e.g., U.S. Pat. No. 6,485,431) in which the compliance of the arterial system is determined from measured arterial pressure and used for calculating the cardiac output as the product of the mean arterial pressure and compliance divided by a time constant. Also known are catheter based methods such as thermodilution (see, e.g., U.S. Pat. No. 4,153,048).

A non-invasive method, known as thoracic electrical bioimpedance, was first disclosed in U.S. Pat. No. 3,340,867 and has recently begun to attract medical and industrial attention [U.S. Pat. Nos. 3,340,867, 4,450,527, 4,852,580, 4,870,578, 4,953,556, 5,178,154, 5,309,917, 5,316,004, 5,505,209, 5,529,072, 5,503,157, 5,469,859, 5,423,326, 5,685,316, 6,485,431, 6,496,732 and 6,511,438; U.S. Patent Application No. 20020193689]. The thoracic electrical bioimpedance method has the advantages of providing continuous cardiac output measurement at no risk to the patient.

Various methods employing bioimpedance are found in: International Publication Nos. WO2004098376, WO2006087696 and WO2009022330, U.S. Pat. Nos. 6,022,322, 5,615,689 and 5,642,734, and U.S. Published Application Nos. 20030120170, 20060085048 and 20060122540, the contents of which are hereby incorporated by reference.

SUMMARY OF THE INVENTION

According to an aspect of some embodiments of the present invention there is provided a method of diagnosis. The method comprises: acquiring an absolute component and a phase component of an input signal indicative of an impedance of an organ of a subject; determining baseline blood flow of the subject based on the phase component; determining transient changes in blood flow based on at least the absolute component; and displaying the baseline blood flow and the transient changes in blood flow.

According to some embodiments of the invention the invention the method further comprises: acquiring the input signal from the subject, and separating the input signal to an absolute component and a phase component.

According to some embodiments of the invention the absolute component is separated from the input signal by an envelope identifier.

According to some embodiments of the invention the phase component is separated from the input signal by mixing the input signal with a signal indicative of radiofrequency signal transmitted to the subject, to provide a mixed signal, and filtering out a portion of the mixed signal.

According to some embodiments of the invention the method further comprises identifying disturbances in the input signal based on the absolute component, and correcting the baseline blood flow according to the identified disturbances.

According to some embodiments of the invention the method further comprises identifying body movements of the subject based on the absolute component.

According to some embodiments of the invention the method further comprises identifying muscle activity of the subject based on the absolute component.

According to some embodiments of the invention the transient changes in blood flow are characterized by a sub-minute time interval.

According to some embodiments of the invention the separation of the input signal is by an analog processing unit, and the determinations of baseline and the transient changes in blood flow are by a digital processing unit.

According to some embodiments of the invention the method further comprises calculating at least one quantity selected from the group consisting of stroke volume, cardiac output, heart contractility, ventricular ejection time, cardiac index, thoracic fluid content, total peripheral resistance index, and any combination thereof.

According to some embodiments of the invention the calculation of the at least one quantity comprises: calculating a time-dependence of the at least one quantity using the absolute component to provide a first time-dependence, and calculating a time-dependence of the at least one quantity using the phase component to provide a second time-dependence; wherein the method further comprises calculating a correlation coefficient between the first and the second time-dependences, and displaying the at least one quantity responsively to the correlation coefficient.

According to some embodiments of the invention the method further comprises: acquiring an ECG signal from the subject; segmenting the input signal based on the ECG signal to define a time sequence of segments, each corresponding to a single heart beat of the subject; and for at least one of the segments, determining beat morphology of the segment, and determining whether or not to exclude the at least one segment from the diagnosis based on the beat morphology.

According to some embodiments of the invention the method further comprises using the absolute component and the phase component for calculating characteristic capacitance and characteristic resistance associated with the blood flow, and assessing blood vessel compliance, responsively to the characteristic capacitance and the characteristic resistance.

According to an aspect of some embodiments of the present invention there is provided a computer-readable medium having stored thereon a computer program comprising code means for instructing a data processor to carry out the method as described herein.

According to an aspect of some embodiments of the present invention there is provided a system for diagnosis. The system comprises: an input unit configured for receiving from a subject an input signal indicative of an impedance of an organ of the subject; a signal separating unit configured for separating the input signal to an absolute component and a phase component; a processing unit, configured for determining baseline blood flow of the subject based on the phase component, and transient changes in blood flow based on at least the absolute component; and an output unit for displaying the baseline blood flow and the transient changes in blood flow.

According to some embodiments of the invention the system further comprises an electrical oscillator for generating an oscillating signal, a plurality of contact electrodes for transmitting the oscillating signal to the subject and for sensing response of the subject to the oscillating signal, wherein the input unit receives the response.

According to some embodiments of the invention the signal separating unit comprises an envelope identifier for separating the absolute component from the input signal.

According to some embodiments of the invention the signal separating unit comprises a mixer for mixing the input signal with a signal indicative of an oscillating signal transmitted to the subject to provide a mixed signal, and a filter for filtering out a portion of the mixed signal thereby to separate the phase component from the input signal.

According to some embodiments of the invention the processing unit is configured for identifying disturbances in the input signal based on the absolute component, and correcting the baseline blood flow according to the identified disturbances.

According to some embodiments of the invention the processing unit is configured for identifying body movements of the subject based on the absolute component.

According to some embodiments of the invention the processing unit is configured for identifying muscle activity of the subject based on the absolute component.

According to some embodiments of the invention the transient changes in blood flow are characterized by a sub-minute time interval.

According to some embodiments of the invention the signal separating unit is analog, and the processing unit is digital.

According to some embodiments of the invention the processing unit is configured for calculating at least one quantity selected from the group consisting of stroke volume, cardiac output, heart contractility, ventricular ejection time, cardiac index, thoracic fluid content, total peripheral resistance index, and any combination thereof.

According to some embodiments of the invention the processing unit is configured for: calculating a time-dependence of the at least one quantity the absolute component to provide a first time-dependence; calculating a time-dependence of the at least one quantity the phase component to provide a second time-dependence; and calculating a correlation coefficient between the first and the second time-dependences; wherein the output unit displays the at least one quantity responsively to the correlation coefficient.

According to some embodiments of the invention the input unit is configured for receiving an ECG signal from the subject, wherein the processing unit is configured for: segmenting the input signal based on the ECG signal to define a time sequence of segments, each corresponding to a single heart beat of the subject; and for at least one of the segments, determining beat morphology of the segment, and determining whether or not to exclude the at least one segment from the diagnosis based on the beat morphology.

According to some embodiments of the invention the segmentation and the determination of beat morphology are executed separately for the absolute component and for the phase component, wherein the and determining whether or not to exclude the at least one segment comprises comparing between beat morphology as determined from the absolute component with beat morphology as determined from the phase component.

According to some embodiments of the invention the processing unit is configured for calculating characteristic capacitance and characteristic resistance associated with the blood flow, based on using the absolute component and the phase component, and assessing blood vessel compliance, responsively to the characteristic capacitance and the characteristic resistance.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
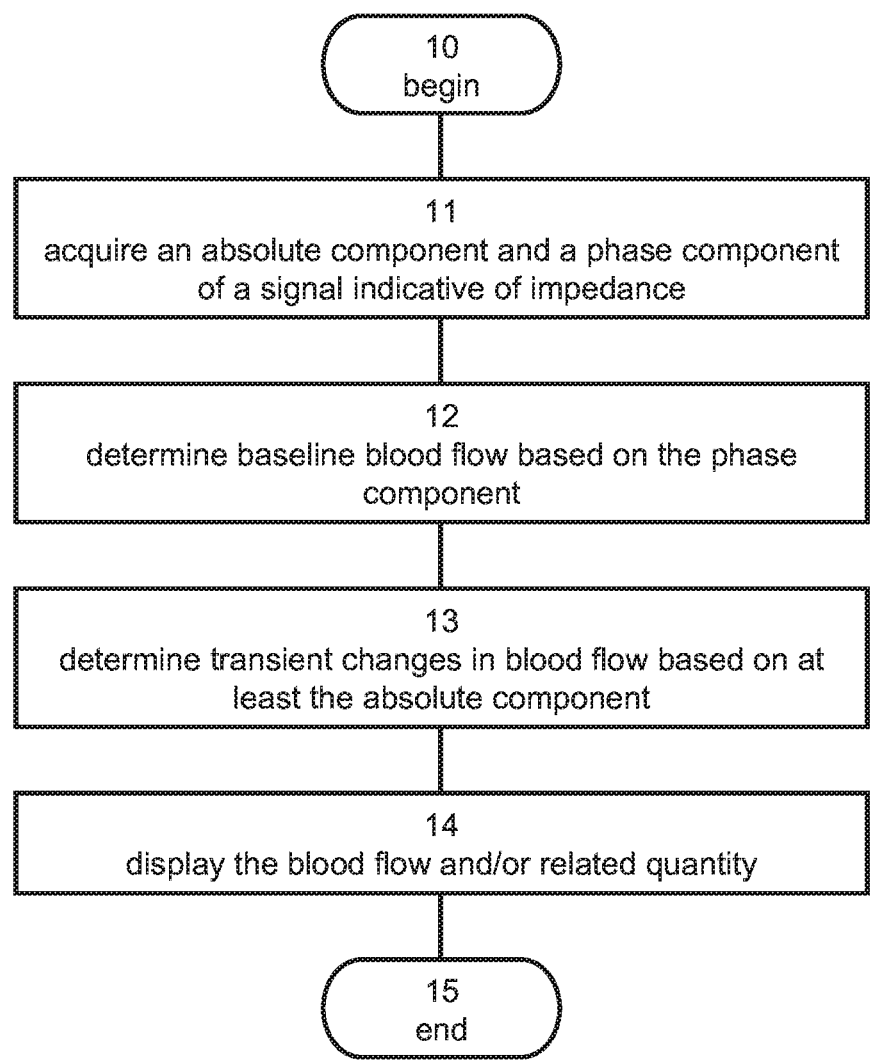
FIG. 1 is a flowchart diagram describing a method of diagnosis according to various exemplary embodiments of the present invention.

The present invention, in some embodiments thereof, relates to diagnosis in medicine and, more particularly, but not exclusively, to system and method for determining blood flow by analyzing electrical signals received from a living body.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Some embodiments of the present invention are described below with reference to flowchart diagrams describing operations which can be performed by the method and system of the present embodiments. It is to be understood that, unless otherwise defined, operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

The method of the present embodiments can be embodied in many forms. For example, it can be embodied in on a tangible medium such as a computer for performing the method. It can be embodied on a computer readable medium, comprising computer readable instructions for carrying out the method. In can also be embodied in electronic device having digital computer capabilities arranged to run the computer program on the tangible medium or execute the instruction on a computer readable medium.

Referring now to the drawings, FIG. 1 is a flowchart diagram describing a method of diagnosis according to various exemplary embodiments of the present invention.

The method begins at 10 and continues to 11 at which at least an absolute component and a phase component of an input signal indicative of an impedance of an organ of a subject is acquired. The organ is preferably the thorax of the subject, but other organs such as, but not limited to, hip, thigh, neck, head, arm, forearm, abdomen, gluteus, leg and foot, are not excluded from the scope of the present invention. The absolute and phase components can be acquired separately, namely via different circuitry channels which separate an input signal to an absolute component and a phase component. This allows the method to process each of these components independently, as further detailed hereinunder.

At any given instance, any electrical signal can be described mathematically as a complex number.

As used herein, the term "absolute component" refers to the absolute value of this complex number, namely the length of the vector which describes the complex number in the complex plane, and the term "phase component" refers to the angle between the vector and the real axis in the complex plane.

Formally, denoting the complex number as A+jB, where A and B represent real numbers and j is a pure imaginary number satisfying $j^2=-1$, the absolute component of the input signal is given by $\sqrt{A^2+B^2}$, and the phase component is given by arctan (B/A).

In various exemplary embodiments of the invention the separation of the input signal into the absolute and phase components is by an analog processing unit. For example, the absolute component can be separated from the input signal by an envelope identifier. The phase component can be separated from input signal by mixing the input signal with a signal indicative of a radiofrequency signal transmitted to the subject and filtering out a portion of mixed signal. A more detailed technique for separating the input signal to its components according to some embodiments of the present invention is described hereinunder.

It was found by the present inventors that a different type of information can be obtained from the phase component and the absolute component for any quantity that is directly or indirectly related to the blood flow. More specifically, in experiments performed by the present inventors, it was found that the phase component of the input signal is less influenced by sudden hemodynamic changes compared to the absolute component of the input signal. The present inventors have therefore devised a technique in which the information extracted from the phase component is combined with the information extracted from the absolute component, in a manner such that the phase component provides information indicative of the baseline of the respective quantity, while the absolute component or a combination (e.g., linear combination) of the phase component and the absolute component provides information indicative of variations with respect to the baseline. Thus, information relevant for relatively long time intervals (e.g., of order of tens of minutes to a few hours) is provided by the phase component of the signal, and information relevant for relatively short time intervals (e.g., of order of seconds to several minutes, and more preferably less than one minute) is provided by the absolute component or a combination of the two components of the signal. The combination of these two types of information provides an accurate as well as responsive diagnosis.

Diagnosis pertaining to quantities that vary by an amount of at least 30% within a time window of less than 10 seconds, or less than 5 seconds or less than 2 seconds or less than 1 second is referred to herein as "real-time diagnosis."

Thus, from 11 the method proceeds to 12 at which a baseline blood flow of the subject is determined based on phase component, and 13 at which transient changes in blood flow are determined based on the absolute component or a combination between the absolute and phase components. The determinations of baseline and transient changes in blood flow are preferably performed by a digital processing unit.

The method can also employ a digital processing unit to calculate one or more blood flow or blood volume related quantities, such as, but not limited to, stroke volume (SV), cardiac output (CO), heart contractility (HC), ventricular ejection time (VET), cardiac index (CI), thoracic fluid content (TFC), total peripheral resistance index (TPRI), and any combination thereof.

The present inventors found that the phase component of the input signal can be utilized for calculating a baseline of the blood flow or blood volume related quantity and the absolute component or a combination of the phase and absolute components of the input signal can be utilized for calculating transient changes in the blood flow or blood volume related quantity.

For example, In some embodiments of the present invention the method calculates HC and VET. Any of these quantities can be calculated separately using the phase and absolute components. Optionally, also the ratio between HC and VET of the subject is calculated separately for the phase and absolute components. This ratio can be utilized as a score to classify septic subjects from a more general group of febrile subjects, where septic subjects have higher ratio compared to febrile but non-septic subjects. Additionally, the relationship between HC and VET can provide insight on other types of subject conditions such as shock due to bleeding, trauma, cardiac causes and the like and help determining and refining fluid resuscitation and fluid optimization treatment.

Figure 8:
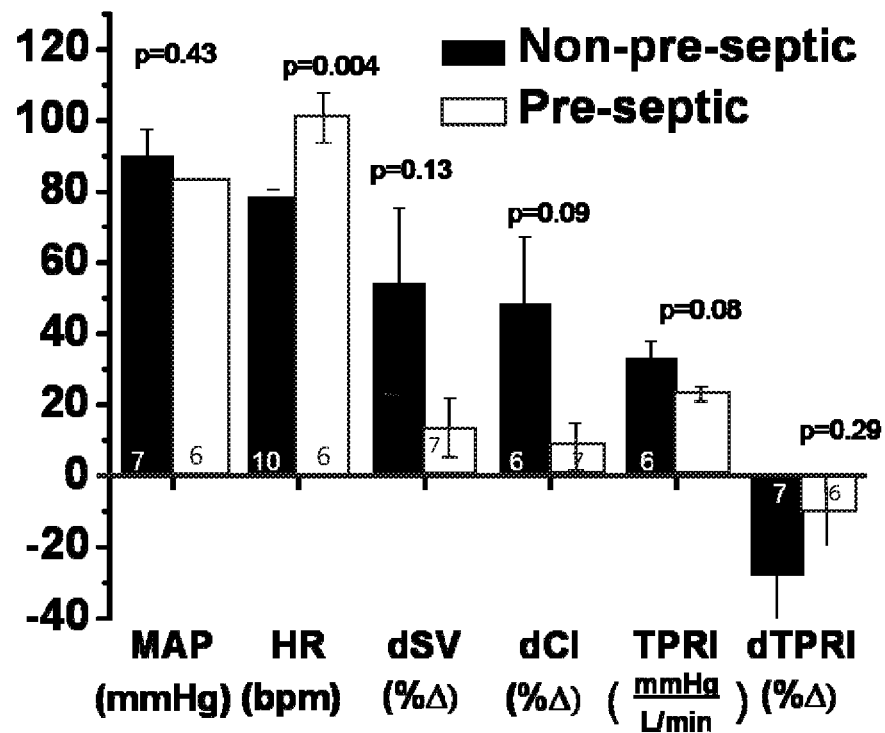
FIG. 8 is a histogram which can be used for diagnosing a subject as septic or non-septic, according to various exemplary embodiments of the present invention.

In some embodiments of the present invention the quantities CI, SV and TPRI are monitored when patient is in sitting position and are again monitored after changing the patient position to supine. The method then calculates the difference in CI (dCI), difference in SV (dSV) and difference in TPRI (dTPRI) between the two positions. The method can display one or more of these differences to allow the physician to diagnose the subject as septic or non-septic (see FIG. 8). Optionally, the method can calculate a score using two or more of three differences, which score can be indicative whether or not the subject can be declared as septic. A representative example of such score is a linear combination, e.g., (dCI+dSV−dTPRI)/3. In this embodiment if the score is below a predetermined threshold (e.g., 10%) the subject is declared as septic, and if the score is above the predetermined threshold the subject is declared as non-septic.

Thus the present embodiments can be used for automatically screening septic patients, e.g., in the ER.

Any of the above scores can also be used for monitoring septic subjects, e.g., during treatment, thereby track their response to treatment.

Figure 9:
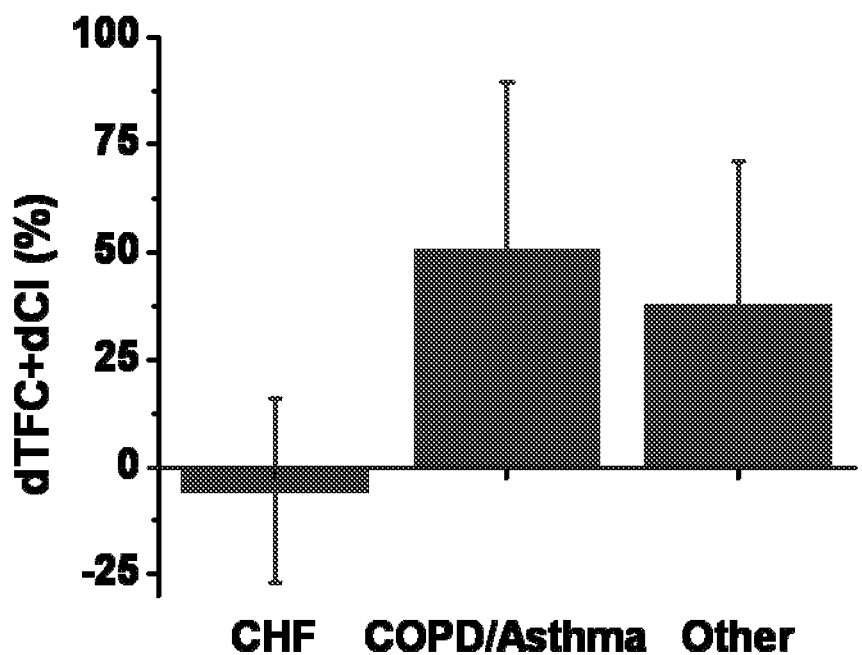
FIG. 9 is a histogram which can be used for diagnosing a subject as having congestive heart failure or a chronic obstructive pulmonary disease, according to various exemplary embodiments of the present invention.

In some embodiments of the present invention the method calculates CI and TFC. Typically, CI is calculated from the phase component, and TFC from the absolute component. The advantage of calculating both CI and TFC is that it allows the physician to distinguish between Congestive Heart Failure (CHF) and Chronic Obstructive Pulmonary Disease (COPD) subjects when shortness of breath is reported. In various exemplary embodiments of the invention the CI and TFC are monitored when the subject is in sitting position and are again monitored after changing the subject's position to supine. The differences in CI (dCI) and difference in TFC (dTFC) between the two positions are then calculated. Based on dCI and dTFC, a score can be established, which score can determine whether the subject suffer from CHF or COPD. A representative example of a score suitable for the present embodiment is a linear combination of dTFC and dCI, e.g., dTFC+dCI. In this embodiment, if the score is below a predetermined threshold (e.g., 10% see, for example, Academic Emergency Medicine 2009; 16(s1): S11) the subject is declared a CHF subject, and if the score is above the predetermined threshold the subject is declared a COPD or a non-CHF subject (see FIG. 9).

The method continues to 14 at which the baseline blood flow or related quantity and/or transient changes in the blood flow or related quantity are displayed, e.g., by means of a display device such as a computer monitor or a printer.

The method ends at 15.

Figure 2:
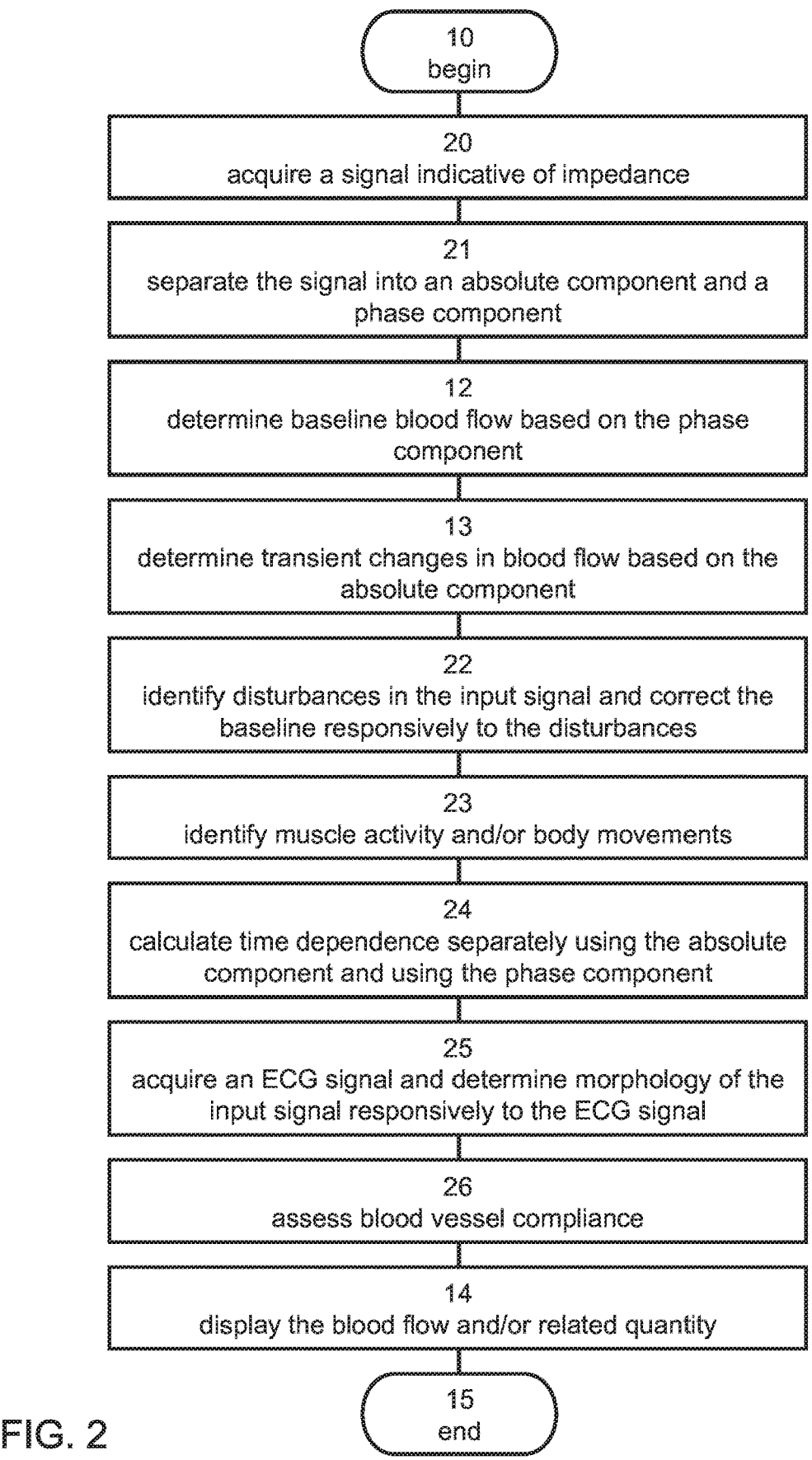
FIG. 2 is a flowchart diagram describing the method of diagnosis in more details, according to some embodiments of the present invention.

FIG. 2 is a flowchart diagram describing the method in more details in accordance with some embodiments of the present invention.

The method begins at 10 and continues to 20 at which the method acquires the input signal from the subject. This is typically achieved by means of an arrangement of electrodes which are attached to the organ of the subject. The electrodes are attached to two or more locations on the organ and are also connected to circuitry that provides an output signal in response to a voltage signal received from the electrodes. The output signal is indicative of the impedance of the tissue between the electrodes. All this is well-known to those skilled in the art of bioimpedance, and is also described in the literature, see, e.g., International Published Application Nos. WO2004/098376 and WO2006/087696, the contents of which are hereby incorporated by reference.

The method continues to 21 at which the input signal is separated to an absolute component and a phase component. The separation can be done by means of different circuitry channels as delineated hereinabove and further detailed hereinunder.

The method proceeds to 12 at which a baseline blood flow of the subject is determined based on phase component, and 13 at which transient changes in blood flow are determined based on the absolute component or a combination of the phase absolute components. The method optionally calculates one or more blood flow or blood volume related quantities, as further detailed hereinabove.

In various exemplary embodiments of the invention the method continue to 22 at which the method identifies disturbances in the input signal and corrects the baseline blood flow or related quantity according to the identified disturbances. It was found by the present inventors that the disturbances in the input signal can be identified using the absolute component. This is because the absolute component has high variability and is therefore prone to detect disturbances in the signal.

The disturbances in the signal can be caused by more than one event. Representative examples include, without limitation muscle activity and body movements. At 23 the method optionally identifies muscle activity, body movements and/or external disturbances based on the absolute component.

In some embodiments of the present invention the method calculates for one or more of the blood flow quantities (e.g., SV, CO, VET, CI, TFC, TPRI, HC, etc.) the time-dependence of the respective quantity. Preferably, the method calculates the time-dependence separately using the absolute component and using the phase component, and displays only one of the calculated time-dependences, based on a predetermined set of criteria. For example, the method can calculate correlation coefficient between the time-dependence as obtained from the phase component and the time dependence as obtained from the absolute component. If the correlation coefficient is above a predetermined threshold, the method can display both time-dependences. If the correlation is low, the method can determine that one or more of the time-dependences is an artifact and decide not to display it. A representative example of a procedure for correlating the two time dependences is provided hereinunder with reference to FIG. 6.

In various exemplary embodiments of the invention the method proceeds to 25 at which the method acquires an ECG signal from the subject and determine the morphology of the input signal responsively to the ECG signal. For example, the method can employ segmentation for segmenting the input signal based on the ECG signal so as to define a time sequence of segments, each corresponding to a single heart beat of the subject; and for at least one of the segments, the method can determine the beat morphology of segment. Once the morphology of the segment is determined, the method can determine whether or not to exclude the respective segment from the diagnosis. A representative example of a procedure for determining beat morphology is provided hereinunder.

The segmentation and determination of beat morphology are preferably executed separately for the absolute component and for the phase component. In this embodiment, the determination whether or not to exclude the segment from the diagnosis comprises comparing between the beat morphology as determined from the absolute component with beat morphology as determined from the phase component.

In various exemplary embodiments of the invention the method proceeds to 26 at which the method assessing blood vessel compliance. The present inventors found that this can be achieved by calculating characteristic capacitance and characteristic resistance associated with the blood flow, and assessing the vessel compliance responsively to the characteristic capacitance and resistance. Specifically, the present inventors found that the outflow of blood from the ventricle into the artery brings about capacitive (C) and restrictive (R) effects, whereby the higher the compliance of the aorta, the higher the C component in the measured signal. Thus, by measuring C separately from R, the present embodiments provide information regarding anatomic and physiologic parameters otherwise not shown by standard bioimpedance measurements. For example, the present embodiments can distinguish between subjects from the standpoint of blood vessel compliance even if the subjects have the same or similar CO. This embodiment can aid in diagnosis of calcified aorta, arterosclerosis, pathologic heamodynamic conditions such as septic shock and shunts.

In some embodiments, R and C are repeatedly measured for the same subject patient at a sufficient sampling rate. The measurements are then used for generating a contour map in the C-R plane. The contours in the map trace a cycle for every heart beat of the subject. The properties of the contours can be used in accordance with preferred embodiments of the present invention for determining the blood flow and blood flow related quantities. This can be done for example, using a look-up table which assign different blood flow values for different shapes of contours.

In some embodiments of the present invention, each of the phase and absolute components is filtered prior to the determination of blood flow or related quantities. The filtration is preferably performed using a digital processing unit and responsively to the physiological condition of the subject. The filtration can be done, for example, by employing the filtering techniques described in International Patent Publication No. 2009/022330 the contents of which are hereby incorporated by reference, separately to the phase and to the absolute components.

In various exemplary embodiments of the invention the filtering is according to a frequency band which is dynamically adapted in response to a change in the physiological condition of the subject. The adaptation of the frequency band to the physiological condition can be according to any adaptation scheme known in the art. For example, one or more parameters of the frequency band (e.g., lower bound, upper bound, bandwidth, central frequency) can be a linear function of a parameter characterizing the physiological condition. Such parameter can be, for example, the number of heart beats per minute.

Figure 3A:
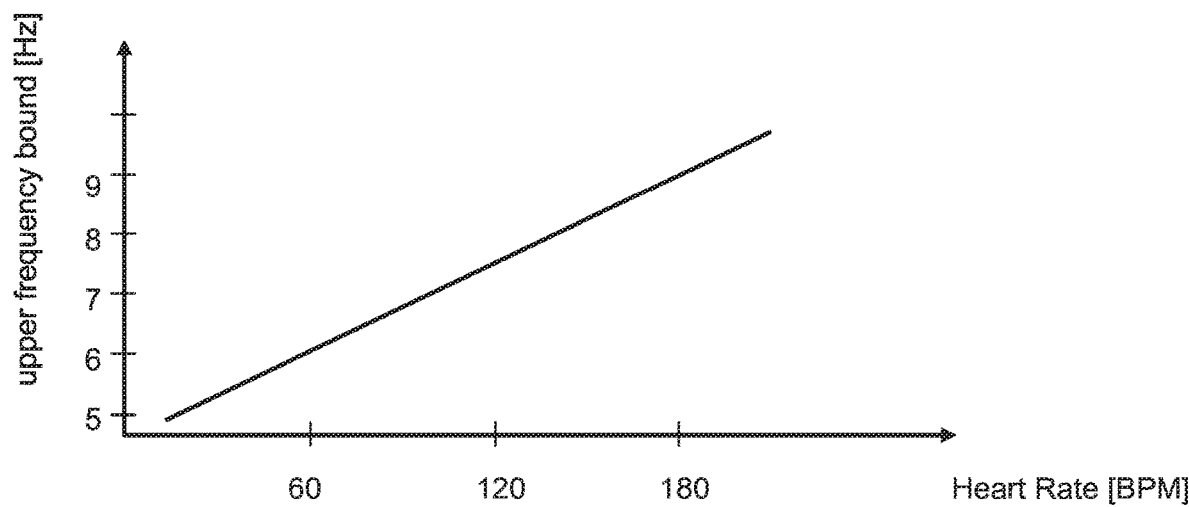
FIGS. 3A and 3B show a representative example of dynamically varying frequency bounds, employed according to embodiments of the present invention.
Figure 3B:
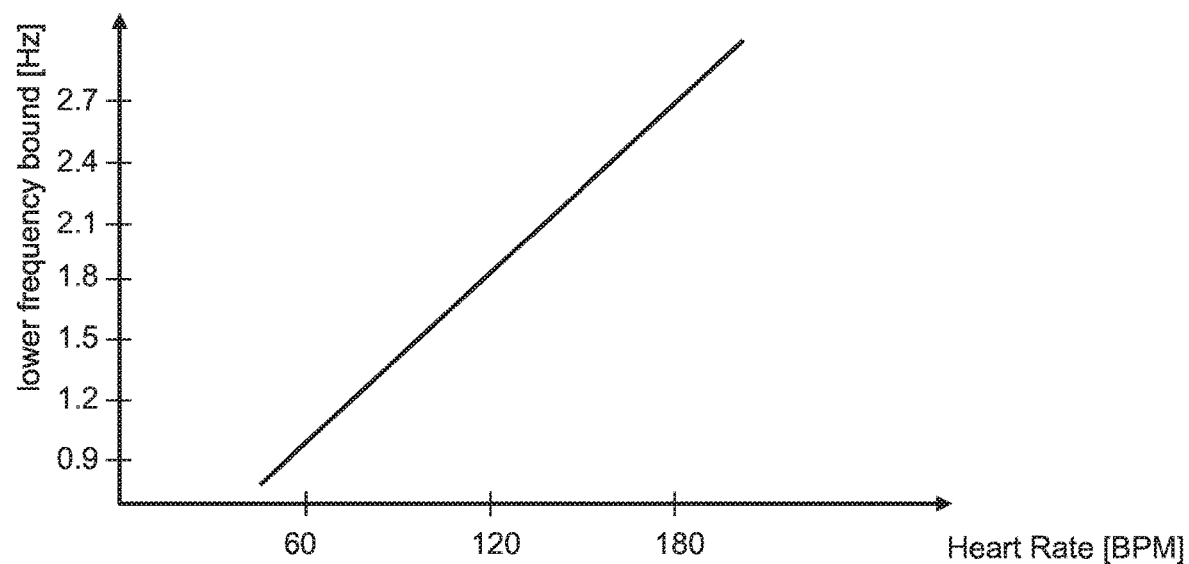

A representative example of a dynamically varying frequency bounds, employed according to some embodiments of the present invention separately to the phase and to the absolute components is illustrated in FIGS. 3A and 3B. Shown in FIGS. 3A and 3B is the functional dependence of the frequency bounds (upper bound in FIG. 3A and lower bound in FIG. 3B) on the heart rate of the subject. As shown in FIG. 3A, the upper bound of the frequency band varies linearly such that at a heart rate of about 60 beats per minute (bpm) the upper bound is about 6 Hz, and at a heart rate of about 180 bpm the upper bound is about 9 Hz. As shown in FIG. 3B, the lower bound of the frequency band varies linearly such that at a heart rate of about 60 the lower bound is about 0.9 Hz bpm and at a heart rate of about 180 bpm the lower bound is about 2.7 Hz.

As used herein the term "about" or "approximately" refers to ±10%.

In some embodiments of the present invention the upper bound approximately equals the function $F_U(HR)$ defined as $F_U(HR)=6+1.5\times[(HR/60)-1]$ Hz, where HR is the heart rate of the subject in units of bpm. In some embodiments, the upper bound equals $F_U(HR)$ at all times, while in other embodiments, the upper bound is set using an iterative process.

In some embodiments of the present invention the lower bound approximately equals the function $F_L(HR)$ defined as $F_L(HR)=0.9\times(HR/60)$ Hz. In some embodiments, the lower bound equals $F_L(HR)$ at all times while in other embodiments the lower bound is set by an iterative process.

Representative examples of iterative process suitable for some embodiments of the present invention are provided hereinunder.

Figure 3C:
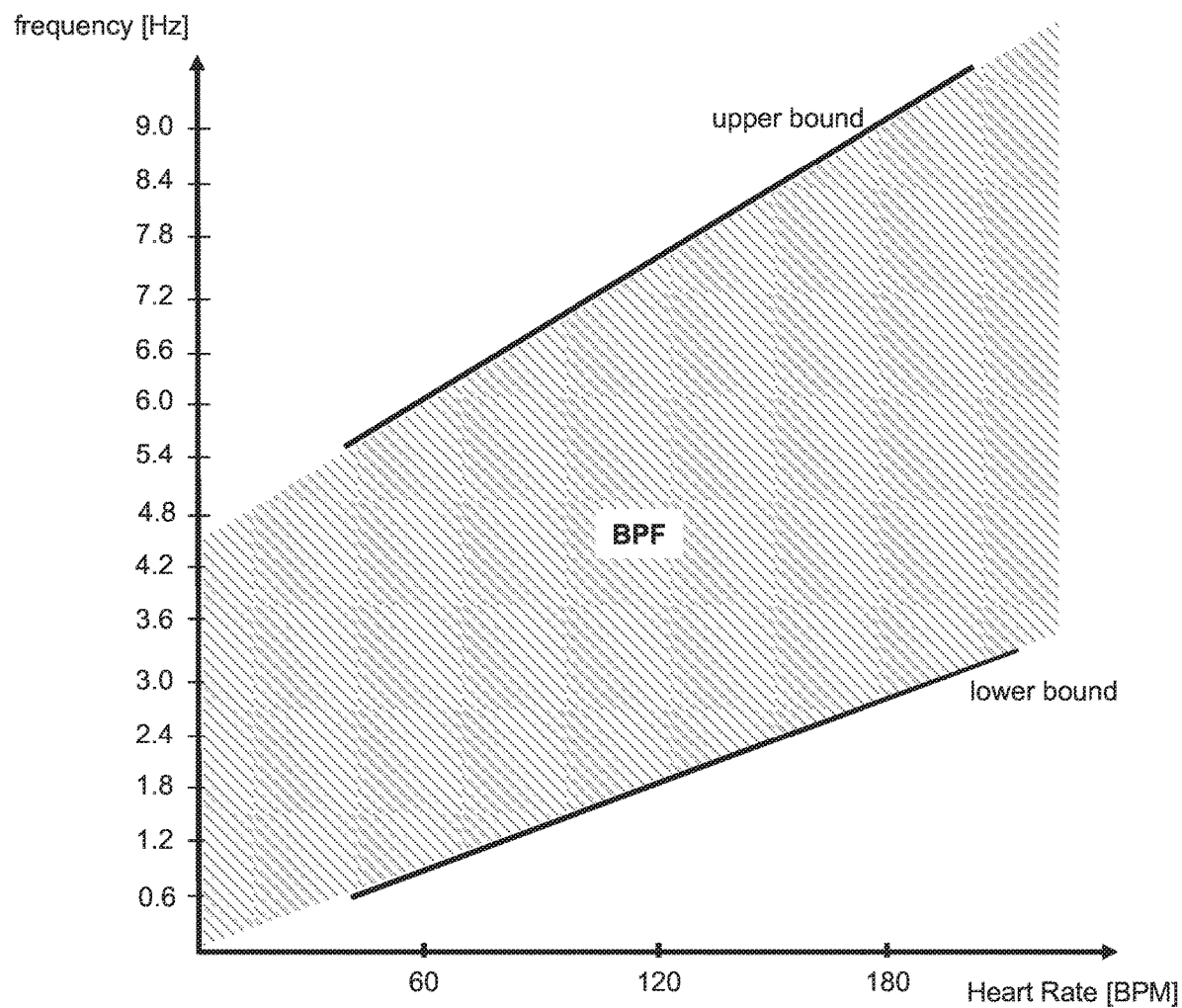
FIG. 3C show a representative example of a dynamically varying frequency band, employed according to embodiments of the present invention.

A dynamically varying band pass filter (BPF) characterized by a dynamically varying upper frequency bound and a dynamically varying lower frequency bound, according to some embodiments of the present invention is illustrated in FIG. 3C. As shown, each heart rate is associated with a frequency band defined by a lower bound and an upper bound. For example, for a heart rate of 60 bpm, FIG. 3C depicts a BPF in which the lower bound is about 0.9 Hz and the upper bound is about 6 Hz.

It is to be understood that the values presented above and the functional relations illustrated in FIGS. 3A-C are exemplary embodiments and should not be considered as limiting the scope of the present invention in any way. In other exemplary embodiments, the functional relations between the frequency band and the physiological condition can have different slopes and/or offsets, or they can be non-linear.

Following is a description of an iterative process for determining the frequency band of the band pass filter which filters to the phase component and separately the absolute component according to some embodiments of the present invention. The iterative process can, in some embodiments, be based a comparison between a value of a physiological parameter as extracted or calculated from the respective filtered component and a value of the same physiological parameter as extracted or calculated from a reference signal, for example, an ECG signal.

The term "physiological parameter" refers to any variable parameter which is measurable or calculable and is representative of a physiological activity, particularly, but not necessarily, activity of the heart. In various exemplary embodiments of the invention the physiological parameter is other than the heart rate per se. The physiological parameter can be a time-related parameter, amplitude-related parameters or combination thereof.

Typically, the filter signal and the reference signal are expressed in terms of amplitude as a function of the time. Thus, time-related parameters are typically calculated using abscissa values of the signals and amplitude-related parameters are is typically calculated using ordinate values of the signals.

Representative of time-related physiological parameters suitable for the present embodiments include, without limitation, systolic time, diastolic time, pre-ejection period and ejection time. A representative example of amplitude-related physiological parameter suitable for the present embodiments includes, without limitation, cardiac contractility, maximal amplitude above zero during a single beat, maximal peak-to-peak amplitude during a single beat, and RMS level during a single beat. Also contemplated are various slopes parameters, such as, but not limited to, the average slope between two points over the signal.

In various exemplary embodiments of the invention the physiological parameter is a ventricular ejection time (VET).

While the embodiments below are described with a particular emphasis to VET as the physiological parameter, it is to be understood that more detailed reference to VET is not to be interpreted as limiting the scope of the invention in any way.

The present inventors discovered that a significant amount of the biological information for a particular subject can be obtained from a frequency range between $F_L(HR)$ and 5.5 Hz, where HR is the heart rate of the subject. It was further discovered by the present inventors that for some medical conditions some of the information can reside between 5.5 Hz and $F_U(HR)$.

The advantage of the comparison between two different techniques for extracting or calculating the same physiological parameter, is that it allows to substantially optimize the upper frequency bound of the of the band pass filter. In various exemplary embodiments of the invention in each iteration of the iterative process, the comparison is repeated. If the comparison meets a predetermined criterion, the upper frequency bound is updated by calculating an average between a low threshold for the upper bound and a high threshold for the upper bound. The lower frequency bound can be a constant bound, e.g., a constant frequency which is from about 0.9 Hz to about 2.7 Hz), or it can be dynamic, e.g., $F_L(HR)$, HR being the heart rate of the subject before or during the respective iteration.

The low and high thresholds for the upper bound can be set in more than one way. In some embodiments, the low and high thresholds are predetermined (namely they determined a priori before the iterative process), in some embodiments, the thresholds are set in a previous iteration of iterative process, in some embodiments one of the thresholds is predetermined and the other threshold is set in a previous iteration of iterative process. In any event, the first iteration is based on two thresholds which are determined a priori before the iterative process. It was found by the inventors of the present invention that, at least initially (i.e., at the first iteration), the first threshold can be about $F_L(40)$, which in various exemplary embodiments of the invention is about 5.5 Hz, and the second threshold can be the calculated value of $F_L(HR)$, HR being the heart rate of the subject before or during the respective iteration.

The predetermined criterion used during the iterations can be, for example, that the results of the two calculations are similar (e.g., within about 40% or 30% or 25% of each other). The predetermined criterion can also relate to the direction of difference between the two calculations. Broadly, for time-related parameters, the upper bound is updated if the value of the parameter as calculated based on the reference signal is higher than value of the parameter as calculated based on the filtered signal, and for amplitude-related parameters the upper bound is updated if the value of parameter as calculated based on the reference signal is lower than the value of the parameter as calculated based on the filtered signal. For slope-related parameters, the upper bound is typically updated if the value of the parameter as calculated based on the reference signal is higher than the value of the parameter as calculated based on the filtered signal.

A Boolean combination between the above criteria can also be used as a criterion. For example, an AND Boolean combination can be employed in which case the upper frequency bound can be updated if the results of the two calculations are similar and the calculation according to the filtered signal indicates an abnormal physiological condition while the calculation according to the reference signal indicates a normal physiological condition.

Figure 4:
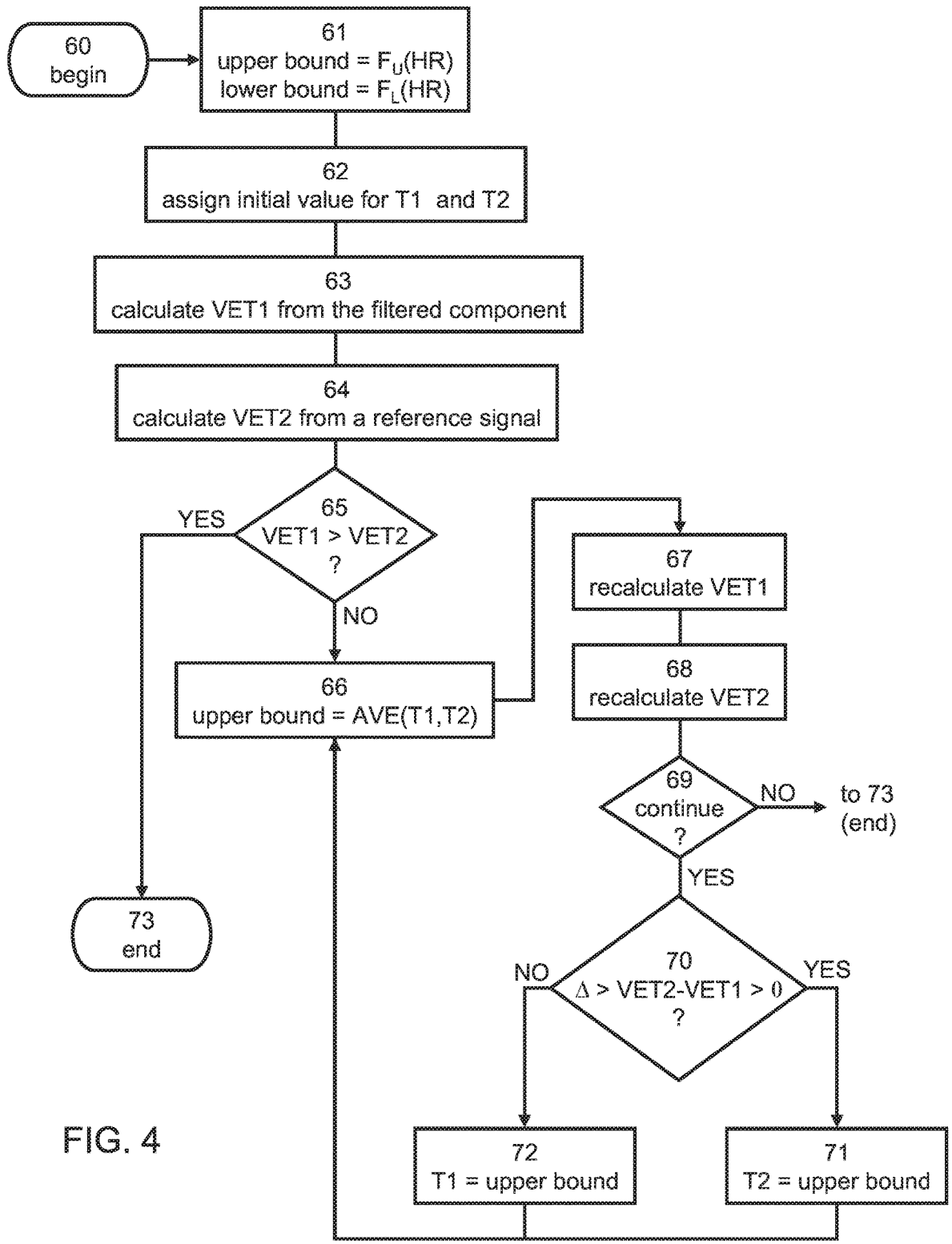
FIG. 4 is a flowchart diagram of an iterative process for selecting a frequency bound, according to various exemplary embodiments of the present invention.

FIG. 4 is a flowchart diagram of an iterative process for selecting the upper frequency bound, according to various exemplary embodiments of the present invention. The description is for a physiological parameter which is VET, but, as stated, it is not intended to limit the scope of the present invention to this type of physiological parameter.

The iterative process begins at 60 and continues to 61 in which the upper frequency bound is set to the value of $F_L(HR)$, HR being the heart rate of the subject before the initiation of the iterative process. The heart rate can be inputted or it can be determined by the process, e.g., from the ECG signal. The process continues to 62 in which initial values are assigned to two frequency thresholds. The frequency thresholds are denoted in FIG. 4 by T1 and T2. In various exemplary embodiments of the invention the initial value of T1 is $F_L(40)$ and the initial value of T2 is the initial upper frequency bound.

The process continues to 63 and 64 in which VET is calculated separately from the filtered respective component (63) and from a reference signal (64), e.g., ECG. The VET as calculated from the respective component is denoted in FIG. 4 VET1 and the VET as calculated from the ECG signal is denoted in FIG. 4 VET2. In the first iteration, the filtered signal from which VET1 is calculated is preferably obtained by filtering the respective component using a band pass filter defined between the upper and lower frequency bounds as initially set at 61.

The process continues to decision 65 in which VET1 and VET2 are compared. If VET1 is higher than VET2, the iterative process continues to 73 where it is terminated. If VET1 is not higher than VET2, the process continues to 66 in which the upper bound is updated to the average AVE of T1 and T2. In various exemplary embodiments of the invention AVE(T1, T2) is the arithmetic mean of T1 and T2 (i.e., AVE(T1, T2)=(T1+T2)/2), this need not necessarily be the case, since, in some embodiments, a different averaging scheme (e.g., a weighted average, a geometric mean, harmonic mean, RMS, etc.) can be employed.

From 66 the process continues to 67 in which VET1 is recalculated but from a signal which is filtered using an updated band pass filter. The lower bound of the updated band pass filter can be the initial lower bound or it can be updated based on the heart rate of the subject immediately before the filtration of the respective component (e.g., according to $F_L$ described above). The upper bound of the updated band pass filter is preferably the updated upper bound. Optionally, the process continues to 68 in which the VET2 is also recalculated from the reference signal. Alternatively, the value of VET2 from 64 can be used.

The process then continues to decision 69 in which the process determines whether or not a predetermined termination criterion is met. If the predetermined termination criterion is met, the iterative process continues to 73 where it is terminated, otherwise the process continues to decision 70 in which VET1 and VET2 are compared. If the deviation between VET1 and VET2 is lower than a predetermined threshold Δ and VET1 is lower than VET2, the process continues to 71 at which the value of the upper bound is assigned to T2, otherwise the process continues to 72 at which the value of the upper bound is assigned to T1.

From 71 and 72 the process loops back to 66 at which an additional iteration begins.

The threshold Δ employed at decision 70 is typically expressed as a fraction of VET2 or a fraction of (VET2−VET1)/VET2. In various exemplary embodiments of the invention Δ=p*VET2, where p<0.5, for example, p=0.4 or p=0.3 or p=0.25.

The termination criterion employed at decision 69 can be for example, a maximal number of iterations. In this embodiment, the process counts the number of iterations and compares them to a predetermined iteration number threshold. If the number of iterations exceeds iteration number threshold the process determines that the termination condition is met and continues to end 73. Typically, but not necessarily, the value of the predetermined iteration number threshold is from about 3 iterations to about 10 iterations, e.g., 5 or 6 iterations.

The termination criterion can also include a comparison of the value of VET1 to a predetermined VET threshold $T_{VET}$, which may be absolute, subject-specific or relative to VET2. It this embodiment, the process compares the value of VET1 to $T_{VET}$. If VET1 is higher than $T_{VET}$ the process determines that the termination condition is met and continues to end 73. Typically, but not necessarily, a relative value of $T_{VET}$ is employed. For example, in various exemplary embodiments of the invention $T_{VET}$=p*VET2 where p<0.5, for example, p=0.4 or p=0.3 or p=0.25.

In any of the above embodiment, the VET (either VET1 or VET2) can be calculated over a single heart beat, or, more preferably, it can be averaged over two or more heart beats. The advantage of using an averaging procedure rather than using a single beat is that it attenuates random disturbances which may be present in the signal during the iterative process. Nevertheless, extraction of the VET from a single beat is not excluded from the scope of the present invention.

For a single heart beat, the calculation of VET can be performed by characterizing the morphology of the beat, identifying two or more identifiable points on the beat and measuring the time between the identified points.

Figure 5A:
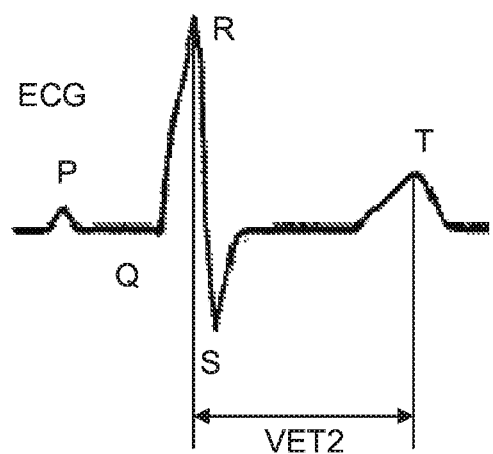
FIG. 5A is a schematic illustration of a procedure for extracting ventricular ejection time from an ECG signal.

FIG. 5A illustrates a procedure for extracting VET2 when the reference signal is an ECG signal. Shown in FIG. 5A is a typical morphology of a single beat of an ECG signal as a function of the time. VET2 can be defined as the time period (difference between the abscissa values) between the R peak and the T peak of the ECG signal.

Figure 5B:
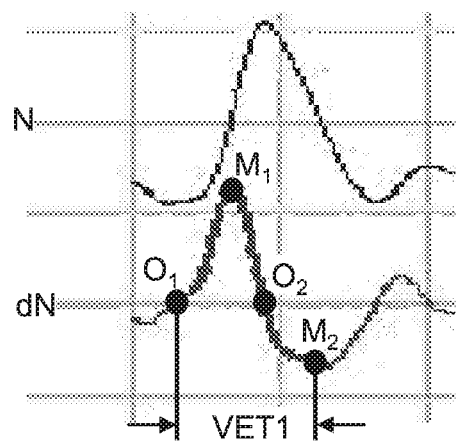
FIG. 5B is a schematic illustration of a procedure for extracting ventricular ejection time from a derivative of a filtered signal according to various exemplary embodiments of the present invention.

When the filtered signal is hemodynamic reactance, the value of VET1 is preferably extracted from the first derivative of the filtered signal. The procedure is illustrated in FIG. 5B, which illustrates a typical morphology of a single beat of the hemodynamic reactance N and its first derivative dN, as a function of the time. As shown, dN has two zeroes $O_1$ and $O_2$ over the beat, with a point of local maximum $M_1$ between the zeroes and a point of local minimum $M_2$ after the second zero. In some embodiments of the present invention VET1 is defined as the time period (difference between the abscissa values) between the first zero $O_1$ and the first minimum $M_2$ after the second zero $O_2$.

The beat morphology of the filtered signal can be characterized by identifying identifiable points on the reference signal and using the time associated with these points (abscissa values) for defining anchor points on the filtered signal.

Figure 5C:
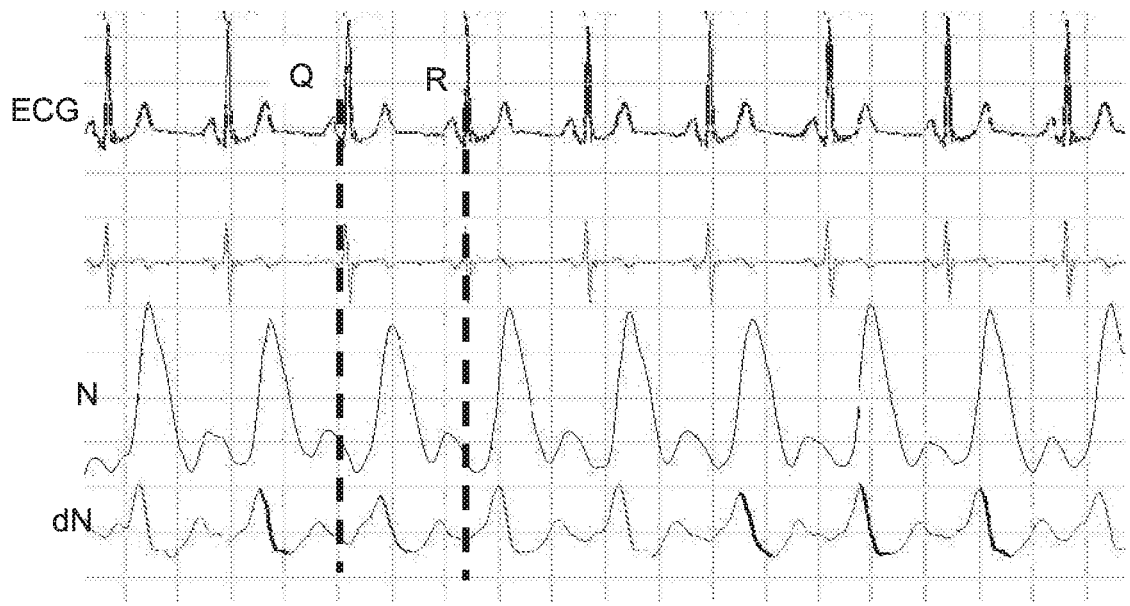
FIGS. 5C and 5D are schematic illustrations of beat morphology characterization procedures, according to various exemplary embodiments of the present invention.

Two exemplary beat morphology characterization procedure of the filtered signal for embodiments in which the respective component is the hemodynamic reactance and the reference signal is the ECG signal are illustrated in FIGS. 5C and 5F.

In FIG. 5C, a single beat of dN (first derivative of the hemodynamic reactance N) is defined between two anchor endpoints: a first (left) endpoint has the abscissa value of the Q peak of the ECG signal, and a second (right) endpoint has the abscissa value of the R peak of the next ECG signal. In other words, a single beat of dN has a width which equals the following sum of five successive intervals over the ECG: QR+RS+ST+TQ+QR.

Figure 5D:
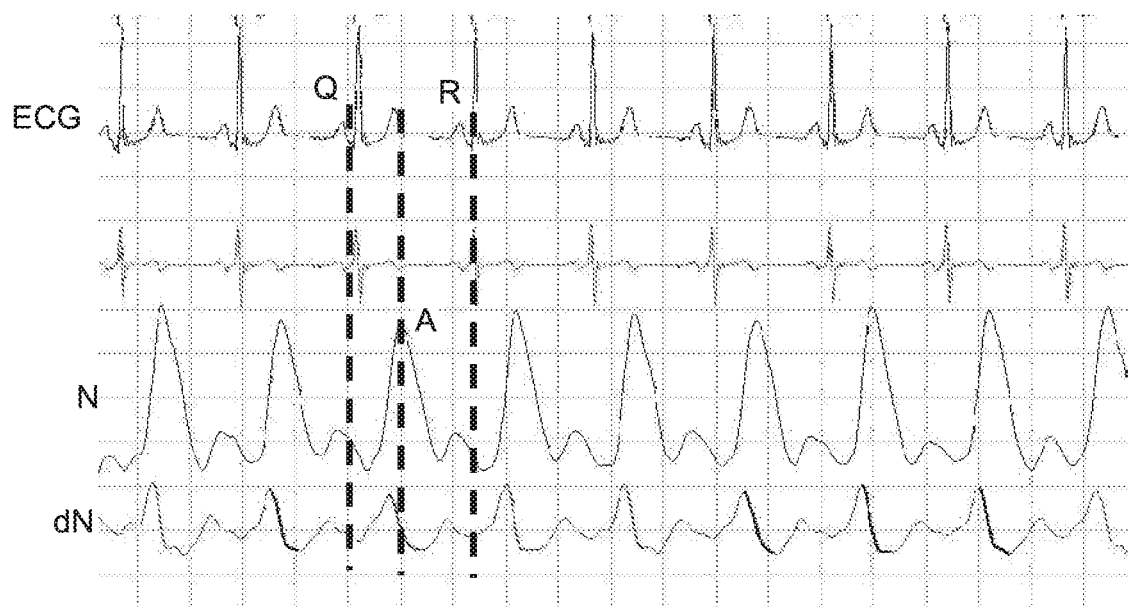

In FIG. 5D, a single beat of dN is defined using three anchor points: the two anchor endpoints as described in FIG. 5C and an intermediate anchor point which has the abscissa value of the global maximum A of the hemodynamic reactance N between the two endpoints.

When the VET is averaged, the calculation can be done in more than one way.

In some embodiments, the same morphology characterization is employed for a plurality of beats over a predetermined interval of the respective signal, so as to provide one local VET for each beat. The VET can be defined as the average of all local VETs. Any averaging procedure can be employed, include, without limitation, arithmetic mean, weighted average, geometric mean, harmonic mean, RMS and the like.

In some embodiments, the morphologies of the beats are averaged over an ensemble of beats in the filtered signal, to provide an average beat morphology, and the VET is be determined by identifying two or more identifiable points on the average beat morphology and measuring the time between the identified points. For example, for each beat in the ensemble, the morphology can be characterized as described above and all the morphologies can be averaged, e.g., point by point. The morphologies can also be averaged in segments. This embodiments is particularly useful when a single beat is defined using more than two anchor points in which case each segment over the beats (between two successive anchor points) can be averaged, e.g., point-by-point. The average beat morphology can then be obtained by stitching the averaged segments. For example, in the embodiment illustrated in FIG. 5D the beat is defined using two intermediate anchor points and an intermediate point. In this embodiment, each beat has a left segment (from the abscissa value of Q to the abscissa value of A) and a right segment (from the abscissa value of A to the abscissa value of R). The left segments of all beats in the ensemble can be averaged to provide a left segment average, and the right segments of all beats in the ensemble can be averaged to provide a right segment average. The average beat morphology can be obtained by stitching the left segment average to the right segment average.

In various exemplary embodiments of the invention the time scale of the beats in the ensemble is adjusted so as to fit all the beats in the ensemble to a single time scale.

The result of this average is a single beat morphology from which VET1 can be extracted as described above. For example, when the first derivative of the hemodynamic reactance is used, the average morphology typically has the shape illustrated in FIG. 5B. VET1 can then be extracted as the time period between $O_1$ and $O_2$. The first derivative of the signal can be calculated before or after averaging. When the first derivative is calculated before the averaging, the averaging procedure described above is performed with respect to the derivative of the signal. When the first derivative is calculated after the averaging, the averaging procedure described above is performed with respect to the signal and the obtained average is then differentiated. Calculation of the first derivative after averaging is preferred from the standpoint of noise reduction.

The predetermined time period over which an averaging procedure is performed to extract the VET typically extends over about 10 heart beats.

Figure 6:
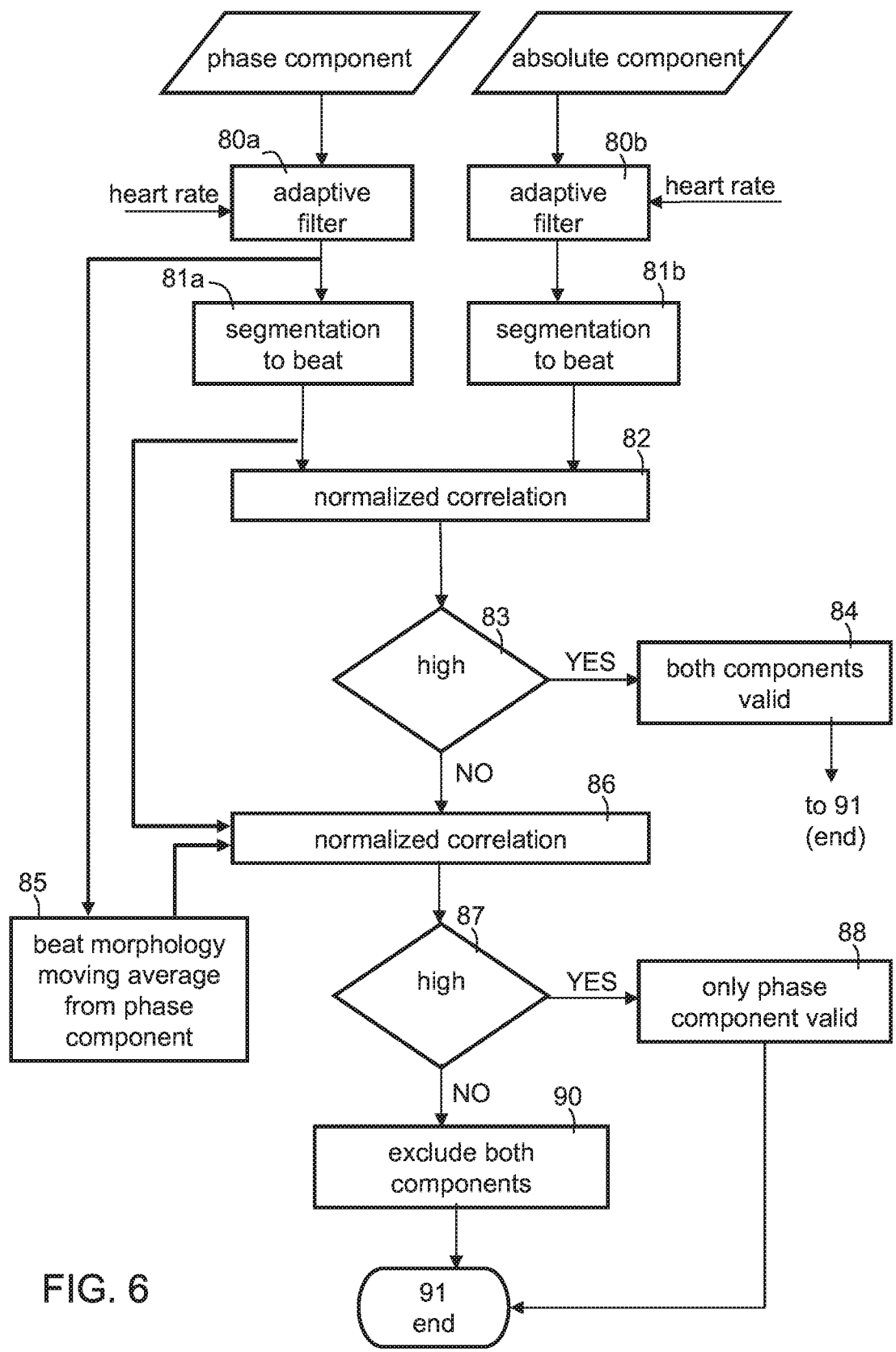
FIG. 6 is a flowchart diagram describing a procedure for correlating the time dependence as obtained from the phase component with the time dependence as obtained from the absolute component, according to various exemplary embodiments of the present invention.

FIG. 6 is a flowchart diagram describing a procedure for correlating the time dependence as obtained from the phase component with the time dependence as obtained from the absolute component, according to various exemplary embodiments of the present invention. Each component is inputted and filtered at 80*a* and 80*b*, for example, using the adaptive procedure described above. After the filtering phase, each component is segmented in time (81*a* and 81*b*) to obtain amplitude morphology for each component. This can be a beat by beat segmentation or an average morphology of several consecutive single beats as further detailed hereinabove.

As the absolute component is more prone to disturbances and the phase component is more stable, the morphology of the absolute component is compared to the morphology of the phase component by testing 83 the correlation 82 between them. The correlation is preferably normalized correlation. For example, the method can first calculate the covariance C between the morphology vector as determined from the phase component and the morphology vector as determined from the absolute component. Thereafter, the method can calculate the diagonal, diagC, of the covariant matrix and normalize the covariance matrix C using the matrix sqrt(diagC·diagC$^T$) which is formed by multiplying the column vector diagC by row vector diagC$^T$ and taking the square root of each element in the thus formed multiplication. The resulting normalized covariance $C_N$ is then given by $C_N=C/\mathrm{sqrt}(\mathrm{diag}C \cdot \mathrm{diag}C^T)$, where the division should be understood as an element-by-element division. The correlation coefficient can then be defined as one of the non diagonal elements in the normalized covariance matrix $C_N$.

If the correlation is above or equal a predetermined threshold $C_{tr}$, the procedure determines 84 that both components are substantially without disturbances and are valid for further processing. If on the other hand, the correlation is below $C_{tr}$, the procedure determines that the morphology of the absolute component is distorted. In this case, the procedure checks whether the morphology as determined from the phase component is also distorted. This can be achieved by calculating 85 a moving average beat morphology from the phase component, and correlating 86 between the beat morphology as calculated at 81*a* and the beat morphology as calculated at 85. The correlation 86 can be a normalized correlation as described above. The procedure then tests 87 the value of the correlation coefficient. If the correlation equals or above $C_{tr}$ the procedure determines 88 that the only phase component is valid for further processing and excludes the absolute components from further processing. If the correlation is below $C_{tr}$ the procedure excludes 90 both components from further processing. A typical value for a correlation threshold $C_{tr}$ is about 0.8. This value is particularly useful when the correlation is normalized.

The procedure ends at 91.

The above procedure can be used to determine at any given time which of the information obtained from the two components is valid for further analysis hence significantly reduces the noise.

For example, when it is desired to calculate SV, the following procedure can be employed.

If both components are valid, SV can be calculated using one of the following formulae:

$$SV=a_1 \cdot [SV]_p + b_1 \cdot d[SV]_a, \text{ or}$$

$$SV=a_1 \cdot [SV]_p + b_1 \cdot d[SV]_a + c_1 \cdot d[SV]_p, \text{ or}$$

$$SV=a_1 \cdot [SV]_p + k_1 \cdot [SV]_a + b_1 \cdot d[SV]_a + c_1 \cdot d[SV]_p, \text{ or}$$

where:

$a_1$, $k_1$, $b_1$ and $c_1$ are weight parameters which can be determined empirically;

$[SV]_p$ is the stroke volume as calculated from the phase component;

$[SV]_a$ is the stroke volume as calculated from the absolute component;

$d[SV]_a$ is defined as $[SV]_a(n)-[SV]_a(n-1)$, where $[SV]_a(n-1)$ and $[SV]_a(n)$ are the stroke volume as calculated from the absolute component at two successive valid beats (beat Nos. n and n−1 in the present example); and $d[SV]_p$ is defined as $[SV]_p(n)-[SV]_p(n-1)$, where $[SV]_p(n-1)$ and $[SV]_p(n)$ are the stroke volume as calculated from the phase component at two successive valid beats (beat Nos. n and n−1 in the present example).

If only the phase component is valid, SV can be calculated using the formula $$SV=a_2 \cdot [SV]_p + b_2 \cdot d[SV]_p,$$

where $a_2$ and $b_2$ are weigh parameters which can be determined defined empirically.

In the above procedure, each of $[SV]_a$ and $[SV]_p$ can be calculated from the respective component of the signal using any technique known in the art. In preferred embodiments, the calculation is according to the teachings of International Published Application No. WO2004/098376 or International Published Application No. WO2006/087696, the contents of which are hereby incorporated by reference.

The beat morphologies as determined separately from the phase and absolute components can be used for extracting heart contractility HC. The heart contractility is preferably represented by the first derivative dX/dt of the reactance with respect to the time.

If both components are valid, the method preferably employs one of the following formulae for calculating HC:

$$HC=a_3 \cdot [HC]_p + b_3 \cdot d[HC]_a, \text{ or}$$

$$HC=a_3 \cdot [HC]_p + b_3 \cdot d[HC]_a + c_3 \cdot d[HC]_p, \text{ or}$$

$$HC=a_3 \cdot [HC]_p + k_3 \cdot [HC]_a + b_3 \cdot d[HC]_a + c_3 \cdot d[HC]_p,$$

where:

$a_3$, $k_3$, $b_3$ and $c_3$ are weight parameters which can be determined empirically;

$[HC]_p$ is the first derivative of the reactance with respect to the time as calculated from the phase component;

$[HC]_a$ is the first derivative of the reactance with respect to the time as calculated from the absolute component;

$d[HC]_a$ is defined as $[HC]_a(n)-[HC]_a(n-1)$, where $[HC]_a(n-1)$ and $[HC]_a(n)$ are the first derivative of the reactance with respect to the time as calculated from the absolute component at two successive valid beats (beat Nos. n and n−1 in the present example); and $d[HC]_p$ is defined as $[HC]_p(n)-[HC]_p(n-1)$, where $[HC]_p(n-1)$ and $[HC]_p(n)$ are the first derivative of the reactance with respect to the time as calculated from the phase component at two successive valid beats (beat Nos. n and n−1 in the present example).

If only the phase component is valid, HC can be calculated using the formula $$HC=a_4 \cdot [HC]_p + b_4 \cdot d[HC]_p,$$

where $a_4$ and $b_4$ are weigh parameters which can be determined defined empirically.

The beat morphologies as determined separately from the phase and absolute components can be used for extracting VET.

If both components are valid, the method preferably employs one of the following formulae for calculating VET:

$$VET=a_5 \cdot [VET]_p + b_5 \cdot d[VET]_a, \text{ or}$$

$$VET=a_5 \cdot [VET]_p + b_5 \cdot d[VET]_a + c_5 \cdot d[VET]_p, \text{ or}$$

$$VET=a_5 \cdot [VET]_p + k_5 \cdot [VET]_a + b_5 \cdot d[VET]_a + c_5 \cdot d[VET]_p,$$

where:

$a_5$, $k_5$, $b_5$ and $c_5$ are weight parameters which can be determined empirically;

$[VET]_p$ is VET as calculated from the phase component (e.g., according to the procedure described above with reference to FIGS. 5A and 5B);

$[VET]_a$ is VET as calculated from the absolute component (e.g., according to the procedure described above with reference to FIGS. 5A and 5B);

$d[VET]_a$ is defined as $[VET]_a(n)-[VET]_a(n-1)$, where $[VET]_a(n-1)$ and $[VET]_p(n)$ are VET as calculated (e.g., according to the procedure described above with reference to FIGS. 5A and 5B) from the absolute component at two successive valid beats (beat Nos. n and n−1 in the present example); and $d[VET]_p$ is defined as $[VET]_p(n)-[VET]_p(n-1)$, where $[VET]_p(n-1)$ and $[VET]_p(n)$ are VET as calculated (e.g., according to the procedure described above with reference to FIGS. 5A and 5B) from the phase component at two successive valid beats (beat Nos. n and n−1 in the present example).

If only the phase component is valid, VET can be calculated using the formula $$\text{VET} = a_6 \cdot [\text{VET}]_p + b_6 \cdot d[\text{VET}]_p,$$

where $a_6$ and $b_6$ are weigh parameters which can be determined defined empirically.

The extracted HC and VET can further be used by the method for calculating the ratio between HC and VET, for example, for the purpose of classifying septic subjects from febrile subjects, as further detailed hereinabove.

Many other blood flow and blood volume quantities can be calculated in a similar manner, and the ordinarily skilled person, provided with the details described herein would know how to adjust the procedures and formulae for other blood flow and blood volume quantities, including, without limitation, CO, CI, TFC, TPRI, dCI, dTFC, dTPRI, and the like. For example, CO can be calculated by multiplying the stroke volume SV by the heart rate of the subject, CI can be calculated by dividing CO by the surface area of the subject's body, TFC can be directly from the phase and absolute components since the impedance is inversely proportional to the amount of body fluid in the organ, and TPRI can be calculated by dividing the mean blood pressure (MBP) by CI.

Figure 7:
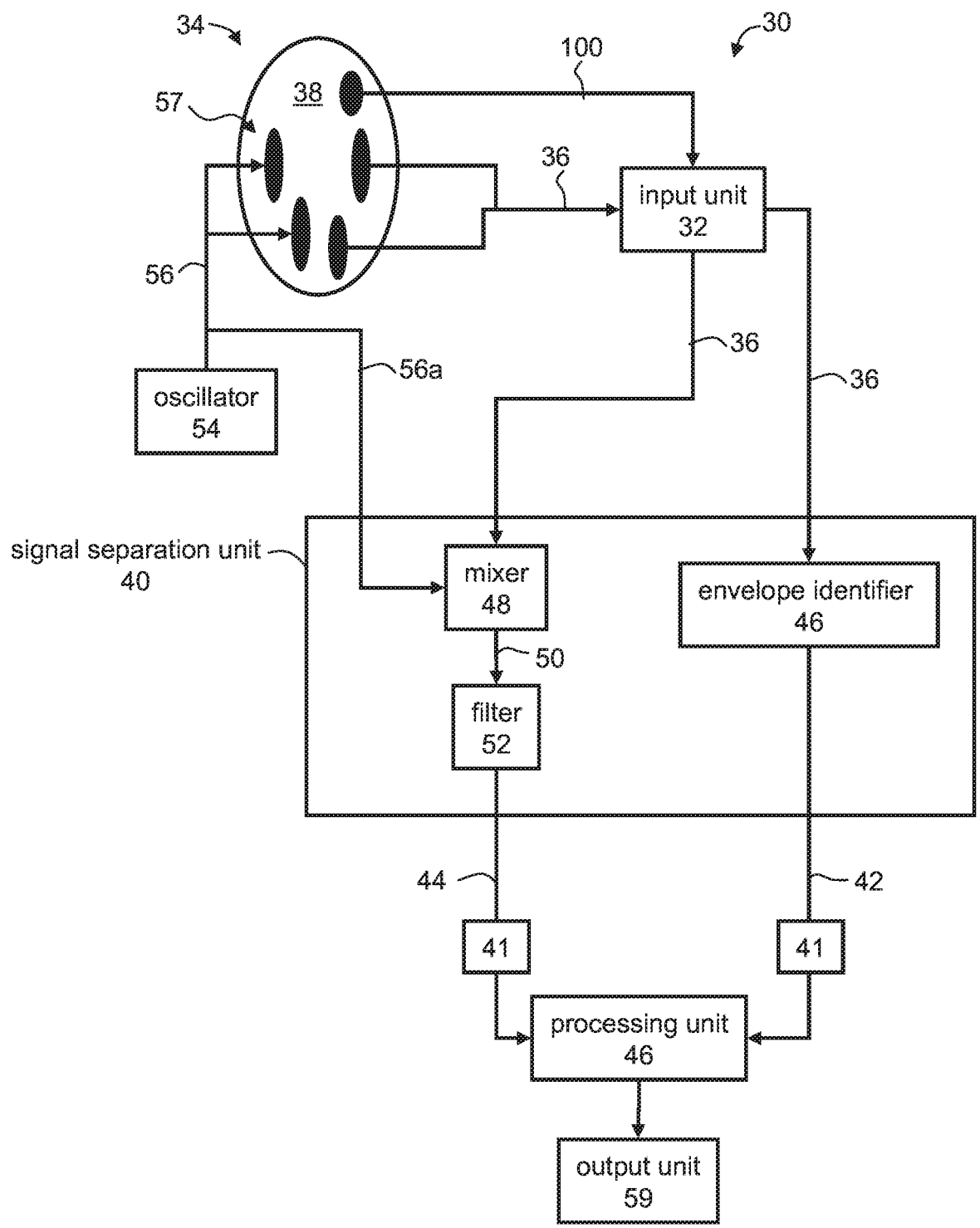
FIG. 7 is a schematic illustration of a system for diagnosis, according to various exemplary embodiments of the present invention.

Reference is now made to FIG. 7 which is a schematic illustration of a system 30 for diagnosis, according to various exemplary embodiments of the present invention. System 30 comprises an input unit 32 which receives from a subject 34 an input signal 36 indicative of an impedance of an organ 38 of subject 34.

In various exemplary embodiments of the invention system 30 comprises an electrical oscillator 54 which generates an oscillating signal 56, and a plurality of contact electrodes 57 for transmitting oscillating signal 56 to subject 34 and for sensing the response of subject 34, wherein input unit 32 receives the response in the form of input signal 36.

System 30 further comprise a signal separating unit 40 which separate input signal 36 to an absolute component 42 and a phase component 44. In various exemplary embodiments of the invention signal separating unit 40 is an analogue processing unit. The separation of input signal 36 can be done by any technique known in the art. For example, in some embodiments, signal separating unit 40 comprises an envelope identifier 46 which separates the absolute component from the input signal, and in some embodiments signal separating unit 40 comprises a mixer 48 which mixes the input signal with a signal 56a indicative of oscillating signal 56 and a filter 52 which filters out a portion of the mixed signal 50 and thus separates the phase component 44 from input signal 36.

System 30 further comprising a processing unit 58 which determine the baseline blood flow of the subject based on phase component 44, and transient changes in blood flow based on absolute component 42 or a combination (e.g., linear combination) of phase component 44 and absolute component 42, as further detailed hereinabove. Processing unit 58 is preferably digital. When unit 40 is analog and unit 58 is digital, communication between unit 40 and unit 58 is preferably via analog-to-digital cards shown schematically at 41.

In some embodiments of the present invention processing unit 58 identifies disturbances in the input signal based on the absolute component, and corrects the baseline blood flow according to the identified disturbances. In some embodiments of the present invention processing unit 58 identifies body movements of the subject based on the absolute component. In some embodiments of the present invention processing unit 58 identifies muscle activity of the subject based on the absolute component.

In some embodiments of the present invention processing unit 58 calculates at least one quantity selected from the group consisting of stroke volume, cardiac output, heart contractility, ventricular ejection time, cardiac index, thoracic fluid content, total peripheral resistance index, and any combination thereof.

System 30 can also comprises an output unit 59 which displays the baseline blood flow and/or transient changes in blood flow. Unit 59 can be, for example, a display device, such as a computer monitor, a printer and the like. Preferably, processing unit 58 calculates one time-dependence of at least one of the quantities from absolute component 42, another time-dependence of the respective quantity from phase component 44, and a correlation coefficient between the two time-dependences. In this embodiment, output unit 59 displays the respective quantity responsively to the correlation coefficient.

In some embodiments of the present invention input unit 32 receives also an ECG signal 100 from subject 34. In this embodiment, processing unit 58 utilizes ECG signal for determining the morphology of input signal 36. For example, unit 58 can segments input signal 36 based on ECG signal 100 and determine the beat morphology of at least one of the segments, as further detailed hereinabove. Processing unit 58 can also determine whether or not to exclude a segment from the diagnosis based on the beat morphology, as further detailed hereinabove. For clarity of presentation, ECG signal 100 is schematically illustrated as originated from a single lead, but the ordinarily skilled person would appreciate that an ECG signal can be established from a plurality of leads. and wherein processing unit is configured for:

In some embodiments of the present invention processing unit 58 calculates characteristic capacitance and characteristic resistance associated with blood flow, based on the absolute and phase components, as further detailed hereinabove. In some embodiments output unit 59 generates a contour map in the C-R plane. In these embodiments unit 58 can provide identifiers to the contours in the map wherein output unit 59 display these identifiers preferably together with the contour map. The identifiers correspond to the shape of the contours and are preferably indicative of the blood flow and blood flow related quantities.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", an and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Examples

Reference is now made to the following examples, which together with the above descriptions illustrate some embodiments of the invention in a non limiting fashion.

Exemplified System

Figure 10:
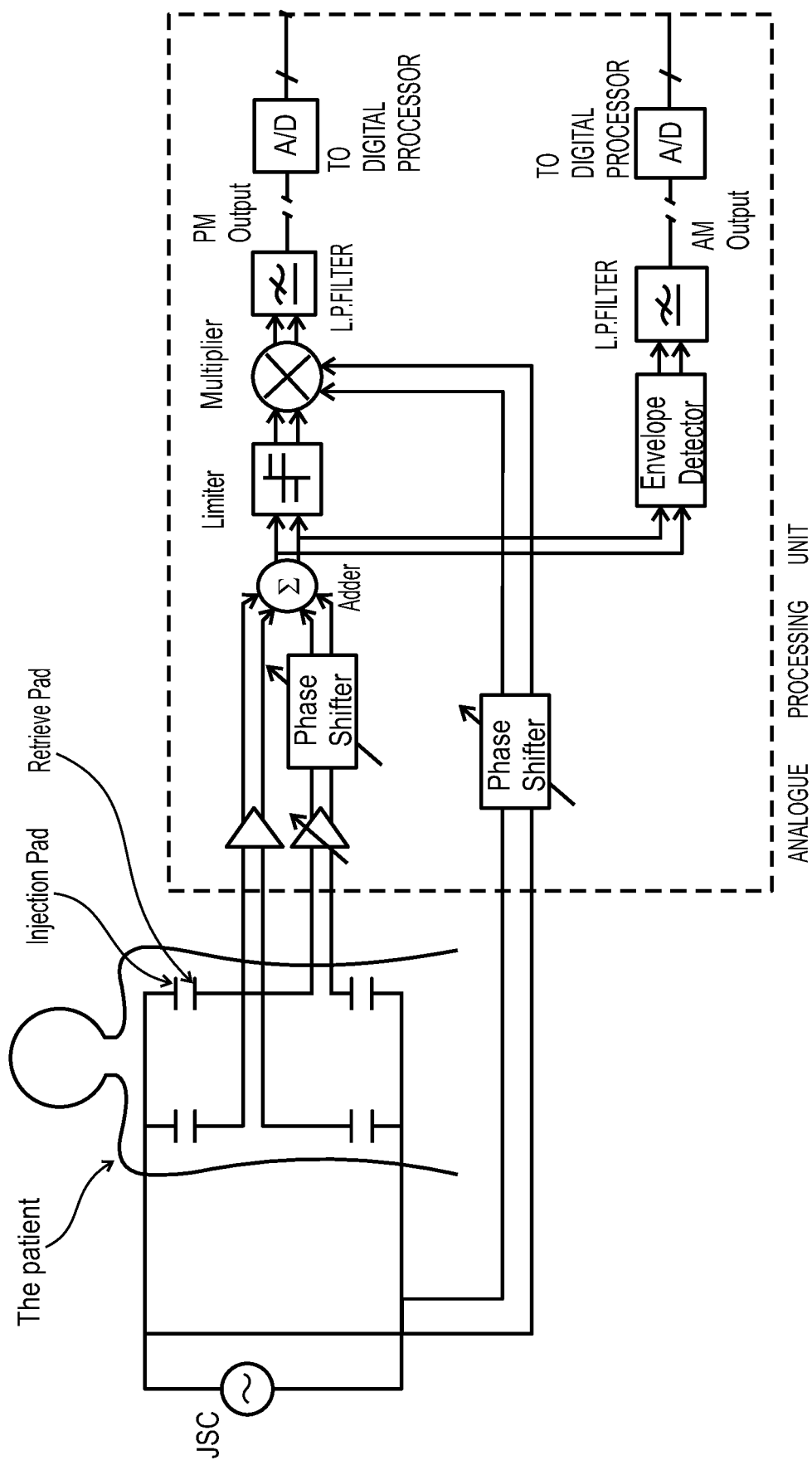
FIG. 10 is a schematic illustration of an exemplified circuitry which can be employed by the method and system of some embodiments of the present invention.

An exemplified circuitry according to some embodiments of the present invention is illustrated in FIG. 10. The exemplified circuitry includes an oscillator JSC which generates a sinusoidal electrical wave. The wave can be at any frequency, preferably radiofrequency. A representative example of a frequency suitable for the present embodiments is 75 KHz, but other frequencies are not excluded. The oscillator preferably has low amplitude and phase noise.

The system also includes an arrangement of electrodes which inject the oscillator's signal into the subject's body, and retrieve signal from the body. In the present embodiments, there are eight electrodes which can be embedded in pads designed to establish good electrical connection between the body and the circuitry. To ensure good and stable connection a gel can be applied on the pads before attaching them to the body. As shown in FIG. 10, there are two groups of electrodes, one group for attaching to the right side of the body, and the other group for attaching to the left side of the body. In the present example, each group of electrodes includes four pads, two for injection and two for sensing signals from the body. The injection pads are connected to the oscillator and the sensing pads are connected to an analogue processing unit.

The analogue processing unit receives the differential signals sensed by the electrodes. The input impedance of the processing unit is preferably very high. In the following, the input impedance is considered as infinite impedance. The purpose of the processing unit is to provide the electrical impedance of the body section by measuring the potential difference between the sensing pads when current is injected into the body by the injection pads. This impedance can be measured in many ways. It is to be understood that more detailed reference to a specific procedure for measuring the impedance is not to be interpreted as limiting the scope of the invention in any way In the processing unit, the signal received by one pair of sensing pads undergoes amplification and filtering, and is then weighed by a complex factor and summed with a second signal, which undergoes amplification and filtering only, in order to generate a single signal for further processing.

The signal is then split to two processing channels. The first channel, referred to as an amplitude detector, detects the envelope of the retrieved signal which is the absolute component of the impedance. The second channel, referred to as a phase detector, detects the phase component of the signal. The analogue signals produced by the analog processing unit are sampled by an analogue to digital converter (A/D) for processing by a digital processing unit.

Resistance and Capacitance Components of the Impedance

Without being bound to any specific theory, the following considerations can be employed for deriving the instantaneous and continuous behavior of the resistance and capacitance components of the impedance.

A constrained sinusoidal current of amplitude I is forced by outer pads and flows through the organ. The impedance Z is measured between the inner pads. The inner pads sense the voltage ZI when the current I is injected by the outer pads. For simplicity it is assumed that Z can be represented by a resistor R and capacitor C in parallel. When the heart goes through its cycle of contraction and expansion, a certain volume of blood is moved from one location to another, and this displacement of blood leads to changes in R, C and Z. Monitoring these changes (along with some parameters of the particular subject) allows measurement of many blood flow related quantities such as the stroke volume.

The instantaneous values of R and C affect the absolute component $|Z|$ and phase component $\varphi$ of the impedance Z Formally, one can write:

$$I = V\left(\frac{1}{R} + j\omega C\right) \quad (1)$$

Where V is the voltage sensed by the inner pads, ω is the angular frequency of the current I, and j is the pure imaginary number $\sqrt{-1}$ indicating that the phase of the current through C leads the phase of the current through R by π/2 radians. Hence:

$$V = IZ = \frac{I}{\frac{1}{R} + j\omega C} = \frac{I}{\sqrt{\left(\frac{1}{R}\right)^2 + (\omega C)^2}} e^{-j\varphi} \quad (2)$$

where $$|V| = \frac{I}{\sqrt{\left(\frac{1}{R}\right)^2 + (\omega C)^2}} \text{ and}$$

$$\varphi = \arctan(\omega CR).$$

Since φ is much smaller than π/2 one can write φ≈ωCR, and solve equation (2) to obtain:

$$R = \frac{|V|}{I}\sqrt{1 + \varphi^2} \quad (3)$$

$$C = \frac{I\varphi}{\omega|V|\sqrt{1 + \varphi^2}} \quad (4)$$

Thus, by measuring the phase component φ and absulute component |V| the present embodiments find R and C, and use therm for measuring blood flow related quantities.

Exemplified Diagnosis

Figure 11:
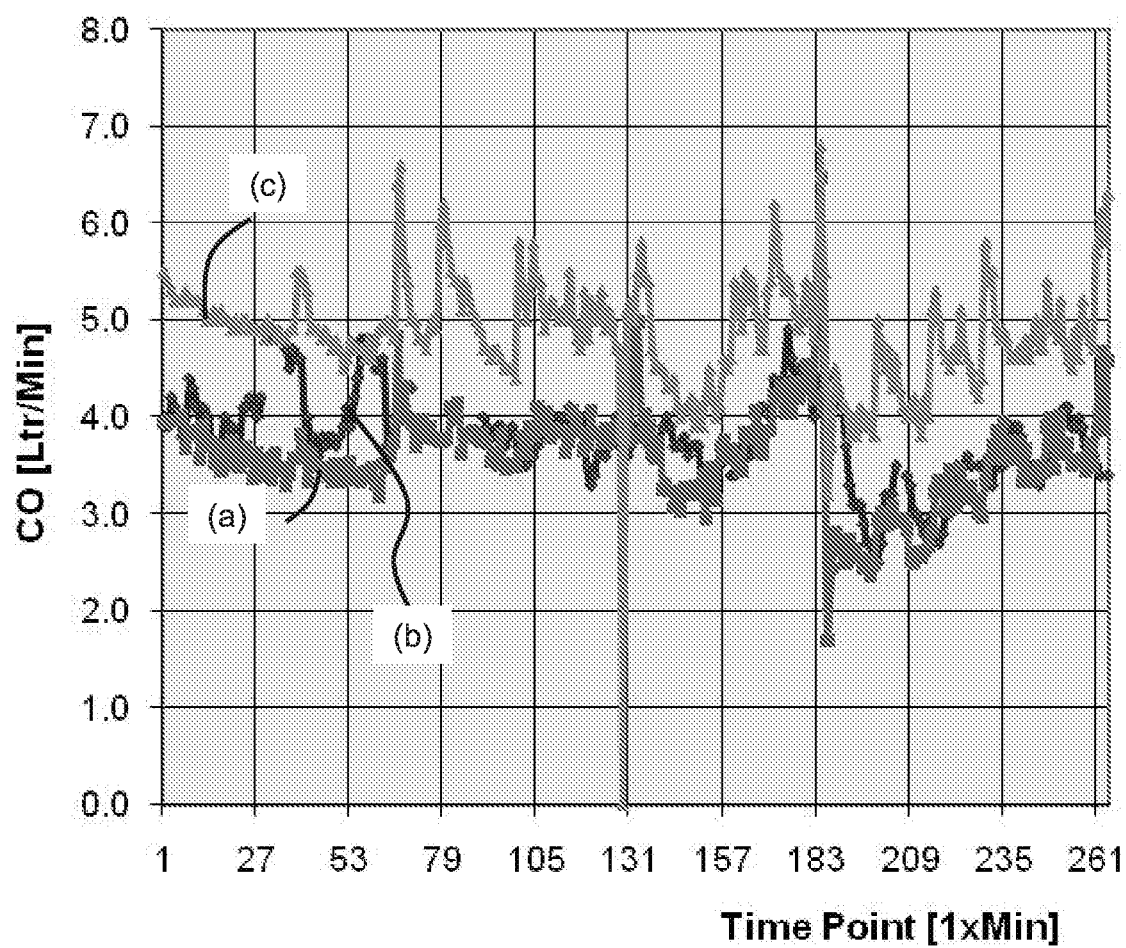
FIG. 11 shows the result of monitoring of a subject for a period of about 260 seconds, in experiment performed according to some embodiments of the present invention.

FIG. 11 shows the result of monitoring of a subject for a period of about 260 seconds. The subject was monitored using three techniques. Monitoring using the technique of the present embodiments is shown by a curve designated (a), monitoring using the gold standard pulmonary artery catheter (Swan Ganz) is shown by a curve designated (b), and CO monitoring using a monitor that analyzes pulse contour of arterial pressure waves acquired via a brachial arterial-line (Edwards Life Sciences, Flotrac-Vigileo) is shown by a curve designated (c).

Around minute 185, a hemodynamic challenge took place. This hemodynamic challenge caused the subject's CO to decrease by about 40% over a few minutes. As shown in the FIG. 11, the technique of the present embodiments provides an accurate CO baseline, generally the same as the baseline provided by the conventional technique (b). On the other hand, the technique of the present embodiments is more responsive than technique (b) when a hemodynamic challenge occurs. The technique of the present embodiments also provides more accurate baseline results compared to the conventional technique (c). Thus, unlike the conventional techniques, the present embodiments combines high accuracy with high responsively.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for displaying a blood flow-related quantity, comprising:
    an input unit having a circuit which is configured for receiving from a subject an input signal indicative of an impedance of at least one organ of the subject;
    a signal separating unit having a circuit which is configured for separating said input signal to an absolute component and a phase component;
    a processing unit, having a dedicated circuitry which is configured for extracting a first time-dependence of the blood flow-related quantity of the subject from said absolute component, and a second time-dependence of said blood flow-related quantity from said phase component, for calculating a correlation coefficient between a morphology of said first time-dependence and a morphology of said second time-dependence, for comparing said correlation coefficient to a predetermined threshold; and
    an output unit having a circuit which is configured for displaying said time-dependences of said blood flow-related quantity;
    wherein said dedicated circuitry is configured to instruct said output unit to display both said time-dependences when said correlation coefficient is above a predetermined threshold.

2. The system according to claim 1, further comprising an electrical oscillator for generating an oscillating signal, a plurality of contact electrodes for transmitting said oscillating signal to the subject and for sensing response of the subject to said oscillating signal, wherein said input unit receives said response.

3. The system according to claim 1, wherein said signal separating unit comprises a mixer for mixing said input signal with a signal indicative of an oscillating signal transmitted to the subject to provide a mixed signal, and a filter for filtering out a portion of said mixed signal thereby to separate said phase component from said input signal.

4. The system according to claim 1, wherein said processing unit is configured for identifying disturbances in said input signal based on said absolute component, and correcting a baseline of said blood flow-related quantity according to said identified disturbances.

5. The system according to claim 1, wherein said processing unit is configured for identifying body movements of the subject based on said absolute component.

6. The system according to claim 1, wherein said processing unit is configured for identifying muscle activity of the subject based on said absolute component.

7. The system according to claim 1, wherein said signal separating unit is analog, and said processing unit is digital.

8. The system according to claim 1, wherein said processing unit is configured for calculating at least one blood flow-related quantity selected from the group consisting of stroke volume, cardiac output, heart contractility, ventricular ejection time, cardiac index, thoracic fluid content, total peripheral resistance index, and any combination thereof.

9. The system according to claim 1, wherein said input unit is configured for receiving an ECG signal from the subject, and wherein said processing unit is configured for:
   segmenting said input signal based on said ECG signal to define a time sequence of segments, each corresponding to a single heart beat of the subject; and
   for at least one of said segments, determining beat morphology of said segment, and determining whether or not to exclude said at least one segment from the diagnosis based on said beat morphology.

10. The system according to claim 9, wherein said segmentation and said determination of beat morphology are executed separately for said absolute component and for said phase component, and wherein said determining whether or not to exclude said at least one segment comprises comparing between beat morphology as determined from said absolute component with beat morphology as determined from said phase component.

11. The system according to claim 1, wherein said processing unit is configured for calculating characteristic capacitance and characteristic resistance associated with said blood flow-related quantity, based on using said absolute component and said phase component, and assessing blood vessel compliance, responsively to said characteristic capacitance and said characteristic resistance.

12. The system according to claim 1, wherein said processing unit is configured for calculating a score for at least one of: (i) classifying a febrile subject as septic or non-septic; and (ii) classifying a subject with Shortness of Breath as having Congestive Heart Failure or Chronic Obstructive Pulmonary Disease.

13. The system according to claim 1, wherein said dedicated circuitry is configured for calculating a moving average beat morphology from said phase component, calculating an additional correlation coefficient describing a correlation between said beat morphology and said moving average beat morphology, and selecting said second time-dependence for displaying when said additional correlation coefficient is above a predetermined threshold.

14. A method of displaying a blood flow-related quantity, comprising:
   using a plurality of contact electrodes for acquiring an input signal from a subject indicative of an impedance of at least one organ of the subject;
   separating said input signal to an absolute component and a phase component;
   using dedicated circuitry configured for extracting a first time-dependence of the blood flow-related quantity of the subject from said absolute component, and a second time-dependence of said blood flow-related quantity from said phase component;
   using said dedicated circuitry configured for calculating a correlation coefficient between a morphology of said first time-dependence and a morphology of said second time-dependence; and
   using said dedicated circuitry configured for selecting, based, at least in part, on said correlation coefficient, either said first time-dependence, said second time-dependence, or both said first and said second time-dependences, and displaying said selected time-dependence or time-dependences of said blood flow-related quantity on a display;
   wherein the method further comprises calculating a moving average beat morphology from said phase component, calculating an additional correlation coefficient describing a correlation between said beat morphology and said moving average beat morphology, and selecting said second time-dependence for displaying when said additional correlation coefficient is above a predetermined threshold.

15. A system for displaying a blood flow-related quantity, comprising:
   an input unit having a circuit which is configured for receiving from a subject an input signal indicative of an impedance of at least one organ of the subject;
   a signal separating unit having a circuit which is configured for separating said input signal to an absolute component and a phase component;
   a processing unit, having a dedicated circuitry which is configured for: (i) extracting a first time-dependence of a blood flow-related quantity of the subject from said absolute component, and a second time-dependence of said blood flow-related quantity from said phase component, (ii) calculating a correlation coefficient between a morphology of said first time-dependence and a morphology of said second time-dependence, (iii) calculating a moving average beat morphology from said phase component, (iv) calculating an additional correlation coefficient describing a correlation between said beat morphology and said moving average beat morphology, and (v) selecting based, at least in part, on said correlation coefficient and said additional correlation coefficient, either said first time-dependence, said second time-dependence, or both said first and said second time-dependences; and
   an output unit having a circuit which is configured for displaying said selected time-dependence or time-dependences of said blood flow-related quantity.

* * * * *